United States Patent
Chen et al.

(10) Patent No.: US 10,448,852 B2
(45) Date of Patent: Oct. 22, 2019

(54) SYSTEM AND METHOD FOR NON-INVASIVE AUTONOMIC NERVE ACTIVITY MONITORING

(71) Applicant: INDIANA UNIVERSITY RESEARCH AND TECHNOLOGY CORPORATION, Indianapolis, IN (US)

(72) Inventors: Peng-Sheng Chen, Indianapolis, IN (US); Shien-Fong Lin, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 125 days.

(21) Appl. No.: 14/649,038

(22) PCT Filed: Dec. 9, 2013

(86) PCT No.: PCT/US2013/073817
§ 371 (c)(1),
(2) Date: Jun. 2, 2015

(87) PCT Pub. No.: WO2014/089549
PCT Pub. Date: Jun. 12, 2014

(65) Prior Publication Data
US 2015/0297104 A1    Oct. 22, 2015

Related U.S. Application Data

(60) Provisional application No. 61/831,817, filed on Jun. 6, 2013, provisional application No. 61/734,771, filed on Dec. 7, 2012.

(51) Int. Cl.
*A61B 5/04* (2006.01)
*A61B 5/0402* (2006.01)
(Continued)

(52) U.S. Cl.
CPC ........ *A61B 5/04001* (2013.01); *A61B 5/0245* (2013.01); *A61B 5/0402* (2013.01);
(Continued)

(58) Field of Classification Search
CPC ... A61B 5/4029; A61B 5/4035; A61B 5/4041; A61B 5/4047; A61B 5/4052; A61B 5/0245; A61B 5/04001
See application file for complete search history.

(56) References Cited

U.S. PATENT DOCUMENTS 5,658,318 A * 8/1997 Stroetmann ........ A61N 1/36114
607/6
7,020,521 B1  3/2006 Brewer et al.
(Continued)

FOREIGN PATENT DOCUMENTS

WO    2002-02007 A1    1/2002
WO    2006094022 A2    9/2006

OTHER PUBLICATIONS

International Search Report and Written Opinion dated Apr. 9, 2014 in connection with PCT/US2013/073817.
(Continued)

*Primary Examiner* — Adam J Eiseman
(74) *Attorney, Agent, or Firm* — Faegre Baker Daniels LLP

(57) ABSTRACT

A system and method for monitoring nerve activity in a subject. The system includes a plurality of electrodes placed in proximity to skin of the subject, an amplifier electrically connected to the electrodes and configured to generate a plurality of amplified signals corresponding to electrical signals received from the subject through the electrodes, and a signal processor. The signal processor applies a high-pass filter to the amplified signals to generate filtered signals from the amplified signals, identifies autonomic nerve activity in
(Continued)

the plurality of filtered signals; and generates an output signal corresponding to the filtered signals. The high-pass filter attenuates a plurality of the amplified signals having frequencies that correspond to heart muscle activity during a heartbeat.

9 Claims, 29 Drawing Sheets

(51) Int. Cl.
| | |
|---|---|
| A61B 5/044 | (2006.01) |
| A61B 5/046 | (2006.01) |
| A61B 5/00 | (2006.01) |
| A61N 1/365 | (2006.01) |
| A61N 1/39 | (2006.01) |
| A61B 5/0245 | (2006.01) |

(52) U.S. Cl.
CPC .............. *A61B 5/044* (2013.01); *A61B 5/046* (2013.01); *A61B 5/04018* (2013.01); *A61B 5/4035* (2013.01); *A61B 5/4836* (2013.01); *A61B 5/4848* (2013.01); *A61B 5/7203* (2013.01); *A61N 1/36514* (2013.01); *A61N 1/3925* (2013.01); *A61B 5/6869* (2013.01); *A61B 5/7425* (2013.01); *A61B 2562/0209* (2013.01)

(56) References Cited

U.S. PATENT DOCUMENTS

| | | | |
|---|---|---|---|
| 2003/0097075 | A1 | 5/2003 | Kuo |
| 2005/0061319 | A1 | 3/2005 | Hartley et al. |
| 2006/0004413 | A1 | 1/2006 | Chen |
| 2006/0106428 | A1 | 5/2006 | Libbus et al. |
| 2006/0241697 | A1 | 10/2006 | Libbus et al. |
| 2006/0253044 | A1 | 11/2006 | Zhang et al. |
| 2008/0294033 | A1 | 11/2008 | Yamazaki |
| 2009/0082831 | A1* | 3/2009 | Paul ............... A61N 1/0456 607/59 |
| 2010/0305637 | A1 | 12/2010 | McCabe et al. |
| 2011/0218415 | A1 | 9/2011 | Peng-Sheng et al. |

OTHER PUBLICATIONS

Tsuchimochi, et al., Direct Measurement of Cardiac Sympathetic Efferent Nerve Activity During Dynamic Exercise, Am. J. Physiol. Heart Cir. Physiol., 2002, 283:H1896-H1906.

European Patent Office, Extended European Search Report, Application No. 13860948.2, dated Jul. 1, 2016.

Zheng, et al., Sudden Cardiac Death in the United States, 1989 to 1998, Circulation, 2001, 104:2158-2163.

Zhou, Spontaneous Stellate Ganglion Nerve Activity and Ventricular Arrhythmia in a Canine Model of Sudden Death, Heart Rhythm, 2008, 5:131-139.

Zipes, et al., Treatment of Ventricular Arrhythmia by Permanent Atrial Pacemaker and Cardiac Sympathectomy, Annals of Internal Medicine, 1968, 68(3):591-597.

Bardy, et al., Amiodarone or an Implantable Cardioverter-Defibrillator for Congestive Heart Failure, The New England Journal of Medicine, 2005, 352(3):225-237.

Bardy, et al., An Entirely Subcutaneous Implantable Cardioverter-Defibrillator, The New England Journal of Medicine, 2010, 363:36-44.

Baron, et al., Sympathetic and Afferent Neurones Projecting into Forelimb and Trunk Nerves and the Anatomical Organization of the Thoracic Sympathetic Outflow of the Rat, Journal of the Autonomic Nervous System, 1995, 53:205-214.

Buxton, et al., A Randomized Study of the Prevention of Sudden Death in Patients with Coronary Artery Disease, The New England Journal of Medicine, 1999, 341:1882-1890.

Buxton, et al., Limitations of Ejection Fraction for Prediction of Sudden Death Risk in Patients with Coronary Artery Disease, Journal of the American College of Cardiology, 2007, 50(12):1150-1157.

Choi, et al., Intrinsic Cardiac Nerve Activity and Paroxysmal Atrial Tachyarrhythmia in Ambulatory Dogs, Circulation, 2010, 121:2615-2623.

Diedrich, et al., Analysis of Raw Microneurographic Recordings Based on Wavelet De-Noising Technique and Classification Algorithm: Wavelet Analysis in Microneurography, IEEE Transactions on Biomedical Engineering, 2003, 50(1):41-50.

Donadio, et al., Skin Sympathetic Adrenergic Innervation: An Immunofluorescence Confocal Study, Ann. Neurology, 2006, 59:376-381.

Einthoven, The Galvanometric Registration of the Human Electrocardiogram, Likewise A Review of the Use of the Capillary-Electrometer in Physiology, Annals of Noninvasive Electrocardiology, 1997, 2(1):93-99.

Ellison, et al., Sympathetic Nerve Pathways to the Human Heart, and Their Variations, American Journal of Anatomy, 1969, 124(2):149-162.

Epstein, et al., ACC/AHA/HRS 2008 Guidelines for Device-Based Therapy of Cardiac Rhythm Abnormalities: Executive Summary, Heart Rhythm, 2008, 5(6):1-22.

Goldenberg, et al., Risk Stratification for Primary Implantation of a Cardioverter-Defibrillator in Patients with Ischemic Left Ventricular Dysfunction, Journal of the American College of Cardiology, 2008, 51(3):288-296.

Hocini, et al., Reverse Remodeling of Sinus Node Function after Catheter Ablation of Atrial Fibrillation in Patients with Prolonged Sinus Pauses, Circulation, 2003, 108:1172-1175.

Jablecki, et al., Literature Review of the Usefulness of Nerve Conduction Studies and Electromyography for the Evaluation of Patients with Carpal Tunnel Syndrome, Muscle & Nerve, 1993, 16:1392-1414.

Jung, et al., Circadian Variations of Stellate Ganglion Nerve Activity in Ambulatory Dogs, Heart Rhythm, 2006, 3:78-85.

Kawashima, The Autonomic Nervous System of the Human Heart with Special Reference to Its Origin, Course, and Peripheral Distribution, Anat. Embryol., 2005, 209:425-438.

Kligfield, et al., Recommendations for the Standardization and Interpretation of the Electrocardiogram, Part 1: The Electrocardiogram and Its Technology, Circulation, 2007, 115:1306-1324.

Langner, et al. Wide Ban Recording of the Electrocardiogram and Coronary Heart Disease, American Heart Journal, 1973, 86(3):308-317.

La Rovere, et al., Baroreflex Sensitivity and Heart-Rate Variability in Prediction of Total Cardiac Mortality After Myocardialyocardial Infarction, The Lancet, 1998, 351:478-484.

La Rovere, et al., Baroreflex Sensitivity and Heart Rate Variability in the Identification of Patients at Risk for Life-Threatening Arrhythmias, Implications for Clinical Trials, Circulation, 2001, 103:2072-2077.

Levy, et al., Maximizing Survival Benefit with Primary Prevention Implantable Cardioverter-Defibrillator Therapy in a Heart Failure Population, Circulation, 2009, 120:835-842.

Mark, et al., Microneurography: A Technique for Assessing Central Neural Effects of Adrenergic Drugs on Sympathetic Outflow in Humans, Journal of Cardiovascular Pharmacology, 1985, 7(Suppl. 8):S67-S69.

Mark, Regulation of Sympathetic Nerve Activity in Mild Human Hypertension, Journal of Hypertension, 1990, 8(Suppl. 7):567-S75.

McCrady, et al., Neural Origin of the Respiratory-Heart Rate Response, American Journal of Physiology—Legacy Content, 1966, 211(2):323-328.

Moss, et al., Unilateral Cervicothoracic Sympathetic Ganglionectomy for the Treatment of Long QT Interval Syndrome, The New England Journal of Medicine, 1971, 285(16):903-904.

(56) References Cited

OTHER PUBLICATIONS

Moss, et al., Improved Survival with an Implanted Defibrillator in Patients with Coronary Disease at High Risk for Ventricular Arrhythmia, The New England Journal of Medicine, 1996, 335(26):1933-1940.
Moss, et al., Prophylactic Implantation of a Defibrillator in Patients with Myocardial Infarction and Reduced Ejection Traction, The New England Journal of Medicine, 2002, 346(12):877-883.
Myerburg, et al., Sudden Cardiac Death: Epidemiology, Transient Risk, and Intervention Assessment, Ann. Intern. Med., 1993, 119:1187-1197.
Narayanan, et al., Frequency and Determinants of Implantable Cardioverter Defibrillator Deployment Among Primary Prevention Candidates with Subsequent Sudden Cardiac Arrest in the Community, Circulation, 2013, 128:1733-1738.
Ogawa, et al., Left Stellate Ganglion and Vagal Nerve Activity and Cardiac Arrhythmias in Ambulatory Dogs with Pacing-Induced Congestive Heart Failure, Journal of the American College of Cardiology, 2007, 50(4):335-343.
Onkka, et al., Sympathetic Nerve Fibers and Ganglia in Canine Cervical Vagus Nerves: Localization and Quantitation, Heart Rhythm, 2013, 10(4):585-591.
Park, et al., Neural Control of Ventricular Rate in Ambulatory Dogs with Pacing-Induced Sustained Atrial Fibrillation, Circ. Arrhythm Electrophysiol., 2012, 5:571-580.
Piccirillo, et al., Power Spectral Analysis of Heart Rate Variability and Autonomic Nervous System Activity Measured Directly in Healthy Dogs and Dogs with Tachycardia-Induced Heart Failure, Heart Rhythm, 2009, 6 (4):546-552.
Ramsaroop, et al., Thoracic Origin of a Sympathetic Supply to the Upper Limb: The 'Nerve of Kuntz' Revisited, Journal of Anatomy, 2001, 199(6):675-682.
Rubart, et al., Mechanisms of Sudden Cardiac Death, Journal of Clinical Investigation, 2005, 115(9):2305-2315.
Salmanpour, et al., Sympathetic Neural Recruitment Patterns During the Valsalva Maneuver, In Engineering in Medicine and Biology Society, EMBC, 2011 Annual International Conference of the IEEE, pp. 6951-6954.
Sanders, et al., Remodeling of Sinus Node Function in Patients with Congestive Heart Failure, Reduction in Sinus Mode Reserve, Circulation, 2004, 110:897-903.
Schalow, et al., Microanatomy and Number of Nerve Fibres of the Lower Intercostal Nerves with Respect to a Nerve Anastomosis. Donor Nerve Analysis. I (IV), Electromyogr. Clin. Neurophysiol., 1992, 32:171-185.
Schroeder, et al., Personality Type and Neural Circulatory Control, Hypertension, 2000, 36:830-833.
Schwartz, et al., Atrami: A Mark in the Quest for the Prognostic Value of Autonomic Markers, European Heart Journal, 1998, 19:1593-1595.
Schwartz, et al., Left Cardiac Sympathetic Denervation in the Management of High-Risk Patients Affected by the Long-QT Syndrome, Circulation, 2004, 109:1826-1833.
Shen, et al. Continuous Low-Level Vagus Nerve Stimulation Reduces Stellate Ganglion Nerve Activity and Paroxysmal Atrial Tachyarrhythmias in Ambulatory Canines, Circulation, 2011, 123:2204-2212.
Shen, et al., Neural Mechanisms of Atrial Arrhythmias, Nature Reviews Cardiology, 2012, 9(1):30-39.
Shen, et al., Patterns of Baseline Autonomic Nerve Activity and the Development of Pacing-Induced Sustained Atrial Fibrillation, Heart Rhythm, 2011, 8(4):583-589.
Shen, et al., Low-Level Vagus Nerve Stimulation Upregulates Small Conductance Calcium Activated Potassium Channels in the Stellate Ganglion, Heart Rhythm, 2013, 10(6):910-915.
Shinohara, et al., Heart Failure Decreases Nerve Activity in the Right Atrial Ganglionated Plexus, J. Cardiovasc. Electrophysiol., 2012, 23(4):404-412.
Tan, et al., Neural Mechanisms of Paroxysmal Atrial Fibrillation and Paroxysmal Atrial Tachycardia in Ambulatory Canines, Circulation, 2008, 118(9):916-925.
Vallbo, et al., Microneurography: How the Technique Developed and Its Role in the Investigation of the Sympathetic Nervous System, J. Appl.. Physiol., 2004, 96:1262-1269.
Victor, et al., Effects of the Cold Pressor Test on Muscle Sympathetic Nerve Activity in Humans, Hypertension, 1987, 9:429-436.
Wallin, et al., Sympathetic Neural Control of Integrated Cardiovascular Function: Insights from Measurement of Human Sympathetic Nerve Activity, Muscle Nerve 2007, 36:595-614.
Hallin, Rolf G. et al., A standardized electrode for percutaneous recording of A and C fibre units in conscious man; Acta Physiol Scand, Dec. 1981; 113(4): 561-3.
Skok, V.I. et al., Human sympathetic electrical activity recorded with skin surface electrodes; Journal of the Autonomic Nervous System, Feb.-Mar. 1985; 12(2-3):261-5.

* cited by examiner

| Dog # | iSGNA vs. iSCNA | iSCNA vs. IVNA | iSGNA vs. IVNA | HR vs. iSCNA | HR vs. iSGNA | HR vs. IVNA |
|---|---|---|---|---|---|---|
| A | r=0.78 p<0.0005 | 0.18 <0.0005 | 0.23 <0.0005 | 0.66 <0.0005 | 0.55 <0.0005 | 0.10 <0.0005 |
| B | r=0.78 p<0.0005 | 0.09 0.001 | 0.004 0.843 | 0.80 <0.0005 | 0.59 <0.0005 | 0.26 <0.0005 |
| C | r=0.77 p<0.0005 | 0.68 <0.0005 | 0.80 <0.0005 | 0.79 <0.0005 | 0.71 <0.0005 | 0.63 <0.0005 |
| D | r=0.71 p<0.0005 | 0.85 <0.0005 | 0.68 <0.0005 | 0.74 <0.0005 | 0.48 <0.0005 | 0.66 <0.0005 |
| E | r=0.54 p<0.0005 | 0.11 <0.0005 | 0.54 <0.0005 | 0.80 <0.0005 | 0.36 <0.0005 | 0.12 <0.0005 |
| F | r=0.59 <0.0005 | 0.58 <0.0005 | 0.68 <0.0005 | 0.63 <0.0005 | 0.55 <0.0005 | 0.43 <0.0005 |
| G | r=0.69 p<0.0005 | 0.56 <0.0005 | 0.53 <0.0005 | 0.76 <0.0005 | 0.69 <0.0005 | 0.49 <0.0005 |

FIG. 21

SYSTEM AND METHOD FOR NON-INVASIVE AUTONOMIC NERVE ACTIVITY MONITORING

CROSS-REFERENCE TO RELATED APPLICATIONS

This application represents the national stage entry of PCT International Application No. PCT/US2013/073817 filed Dec. 9, 2013, which claims priority to U.S. Provisional Application Ser. No. 61/734,771 filed Dec. 7, 2012, and U.S. Provisional Application Ser. No. 61/831,817 filed Jun. 6, 2013, the disclosures of which are incorporated by reference here in their entirety for all purposes.

GOVERNMENT RIGHTS

This invention was made with government support under HL071140 awarded by National Institutes of Health. The government has certain rights in the invention.

BACKGROUND

The present disclosure relates generally to systems and methods for monitoring nerve activity and, in particular, to systems and methods for non-invasive monitoring of nerve activity with cutaneous and subcutaneous electrodes.

Many diagnostic and treatment methods in the fields of medicine and biology rely on measurements of nerve activity in patients and test subjects. Nerve activity in humans and other animals generates electrical signals that are detectable by electronic equipment such as oscilloscopes and other electrical signal processing devices. In order to detect the nerve activity, one or more electrical conductors, or electrodes, are placed in proximity to the nerves being measured. The electrodes may receive the electrical signals for further medical analysis. Various medical treatment methods also use electrodes to deliver electrical signals to the nerves in order to induce a response in the patient.

Cardiac care is one particular area of medical treatment that heavily utilizes measurement of nerve activity. Activity in the autonomic nervous system controls the variability of heart rate and blood pressure. The sympathetic and parasympathetic branches of the autonomic nervous system modulate cardiac activity. Elevated levels of sympathetic nerve activity (SNA) are known to be correlated with heart failure, coronary artery disease, and may be associated with the initiation of hypertension. SNA is also thought to be important as a predictor of heart rhythm disorders, including sudden cardiac death. Therefore, a diagnostic index of "autonomic tone" produced in accordance with measurement of SNA may have considerable clinical value. As known in the art, clinical utilization of autonomic nerve activity is mostly derived from biochemical perturbations like the use of beta-blockers in high blood pressure management. While elevated levels of SNA are known to be correlated with these medical conditions, more precise analysis of the particular electrical signals produced by sympathetic nerves is needed before sympathetic nerve measurement can become a useful diagnostic or prognostic tool. Deficiencies in current technology result in either poor autonomic signal quality or present some difficulty in integrating implantable electronic enhancements (like telemetry, on-chip amplification, storage memory, and motion sensors).

One challenge to measuring nerve activity is that the magnitude of electrical signals in the sympathetic nerves is relatively low, while various other electrical signals present in a patient provide noise that may interfere with isolation and detection of the sympathetic nerve activity. For example, in the human body and the bodies of many animals the electrical activity in the cardiac muscle generates electrical signals with much greater amplitudes than the amplitudes of electrical signals in the nerves. Other muscles in the body can also generate large electrical signals, but the cardiac muscle contractions in a heartbeat occur continuously during any nerve monitoring procedure, and the electrical signals from the cardiac muscle contractions present difficulties in monitoring the lower amplitude signals in the nerve fibers.

In the existing art, a doctor or healthcare professional performs a microneurography procedure on a patient to monitor nerve activity. In microneurography, one or more metal or glass electrodes are inserted into the body of a patient in close proximity to a nerve fiber bundle. The electrodes are formed as thin needles, and the doctor places the needle tip of each electrode in close proximity to the nerve bundle for precise monitoring of the electrical activity in the nerve bundle. The placement of the electrode in close proximity to the nerve enables the electrodes to detect electrical signals that are generated due to nerve activity and to distinguish the nerve activity from the larger electrical signals in the body due to, for example, the cardiac muscle activity. The electrodes receive electrical signals corresponding to the nerve activity in the nerve fiber bundle, and the electrical signals propagate from the electrodes through electrical leads for display and processing using electronic monitoring equipment. Microneurography is an invasive procedure because the electrodes are inserted into the body of the patient. In some scenarios, a doctor punctures the skin of the patient with the needle electrodes to monitor some nerve fibers that are near the surface of the body. In situations where the nerves to be monitored are located deeper within the body, the doctor must perform surgery to implant the electrodes.

While microneurography is effective at monitoring some types of nerve activity, the procedure includes several drawbacks. Because microneurography is an invasive procedure, the patient is typically immobilized to prevent damage to the electrodes, injury to the patient, and to maintain the position of the electrodes in close proximity to the nerve fiber during the monitoring process. During microneurography, a doctor or medical professional inserts the electrodes and removes the electrodes after a relatively short monitoring period, which precludes long-term monitoring of nerve activity and requires that the patient be present in a hospital or other medical facility for nerve monitoring. Additionally, microneurography is not suitable for monitoring many nerves in human patients because the nerves are located in inaccessible regions of the body. For example, microneurography is not approved for use in humans for monitoring nerve fibers, such as the stellate ganglia, which are proximate to the heart, although microneurography is used in studies of cardiac nerve activity in animal test subjects.

Medical professionals, scientists, and patients have a need to monitor nerve activity in a less invasive manner than prior art techniques, such as microneurography, and to perform nerve monitoring in situations where microneurography is impractical. Consequently, improvements to systems and procedures for monitoring nerve activity in human and animal patients would be beneficial.

SUMMARY

The present invention overcomes the aforementioned drawbacks by providing a system and method for monitoring nerve activity in a subject that obviate the limitations of invasive approaches.

In accordance with one aspect of the disclosure, a system for monitoring nerve activity in a subject is provided. The system includes a plurality of electrodes configured to be placed in proximity to skin of the subject, an amplifier electrically connected to the plurality of electrodes and configured to generate a plurality of amplified signals corresponding to a plurality of electrical signals received from the subject through the electrodes, and a signal processor operatively connected to the amplifier. The signal processor is configured to apply a high-pass filter to the plurality of amplified signals to generate a plurality of filtered signals from the plurality of amplified signals, the high-pass filter being configured to attenuate a plurality of the amplified signals having frequencies that correspond to heart muscle activity during a heartbeat, identify nerve activity in the plurality of filtered signals, and generate an output signal corresponding to the nerve activity in the plurality of filtered signals.

In accordance with another aspect of the disclosure, a method for monitoring nerve activity in a subject is provided. The method includes amplifying electrical signals received from a plurality of electrodes that are placed in proximity to skin of the subject to generate a plurality of amplified signals, applying a high-pass filter to the plurality of amplified signals to generate a plurality of filtered signals, the high-pass filter attenuating a plurality of the amplified signals having frequencies that correspond to heart muscle activity during a heartbeat, identifying nerve activity in the plurality of filtered signals, and generating an output signal corresponding to the nerve activity in the plurality of filtered signals.

The foregoing and other advantages of the invention will appear from the following description.

BRIEF DESCRIPTION OF THE DRAWINGS

FIG. 21 shows correlation between nerve activities and heart rate in dog.

DETAILED DESCRIPTION

Figure 1:
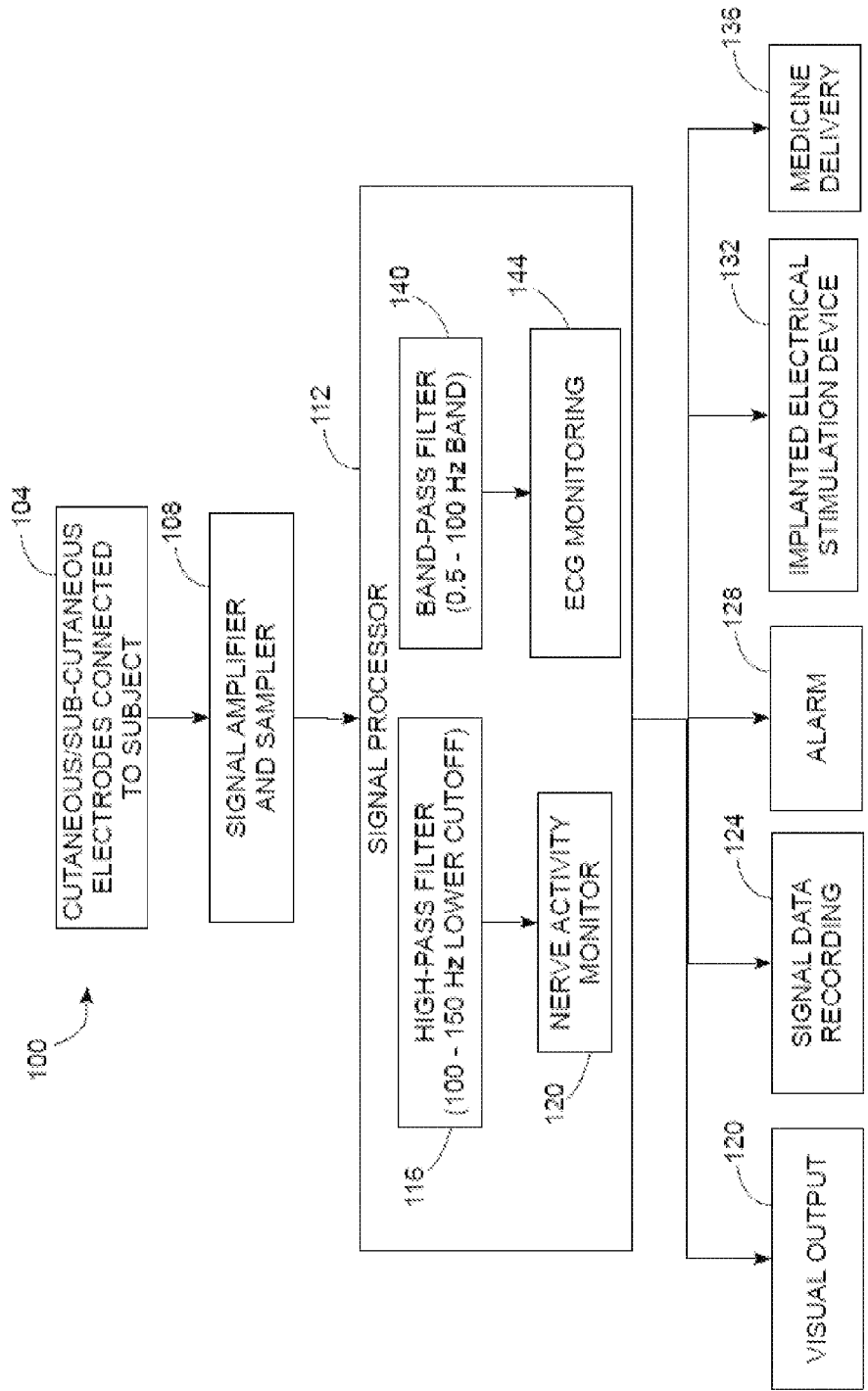
FIG. 1 is a schematic diagram of a system for monitoring electrical activity in nerves that are near the surface of the skin in a subject.

The description below and the accompanying figures provide a general understanding of the environment for the system and method disclosed herein as well as the details for the system and method. In the drawings, like reference numerals are used throughout to designate like elements. As used herein, the term "electrode" refers to an electrical conductor that is configured to establish an electrical contact with biological tissue such as tissue in a patient or test subject. As used herein, the term "arrhythmia" refers to any abnormal activity in the heart of a subject. Examples of arrhythmia include, but are not limited to, tachycardia, bradycardia, atrial flutter, atrial fibrillation, premature contractions, ventricular fibrillation, heart palpitations, and cardiac arrest.

As used herein, the terms "proximity" and "proximate" when used to describe the location of an electrode with respect to the skin of a test subject mean that the electrode is placed in a location on the surface (epidermis) of the skin or under the skin near the hypodermis to enable the electrode to receive electrical signals corresponding to nerves that innervate the skin. For example, in a cutaneous configuration, the electrode is placed in contact with a surface of the skin of the test subject, with some embodiments using an electrical conductor such as a conductive gel to promote electrical contact between the electrode and the skin. In a subcutaneous configuration, the electrode is implanted under the skin of the test subject to enable the electrodes to receive electrical signals in nerves that innervate the hypodermis. In a subcutaneous configuration, the electrode is either in contact with the hypodermis or located within a short distance from the hypodermis, such as under a layer of adipose tissue that is under the skin.

As used herein, the term "cutaneous" as applied to use of electrodes refers to placing electrodes on the surface of the skin of a subject without puncturing the skin of the subject. As described below, the cutaneous electrodes detect electrical activity associated with nerves that are proximate to the skin of the subject, including sympathetic nerves in the autonomic nervous system that innervate the skin.

As used herein, the term "subcutaneous" as applied to use of electrodes refers to placing electrodes entirely underneath the skin with leads from the electrodes being electrically connected to a device that is placed in the body of the test subject, such as an internal pacemaker, defibrillator, or cardiac resynchronization device. The subcutaneous electrodes described herein are different than electrodes that are used in prior art microneurography procedures. First, the subcutaneous electrodes are completely under the skin, with no portion of the electrode or lead extending through the skin. Second, the subcutaneous electrodes do not have to be placed in close proximity to a particular nerve fiber to be used in detection of electrical signals from nerve activity. Third, the subcutaneous electrodes are shaped with a blunt contact surface without the sharp needle tips of microneurographic electrodes, which enables the subcutaneous electrodes to remain under the skin of an ambulatory subject for long term monitoring of nerve activity without injuring the subject. Fourth, the metal housing of an implanted device can be used to house subcutaneous electrodes in some embodiments. In the latter situation, no additional electrodes are needed.

In both the cutaneous and subcutaneous configurations described above, the electrodes are located proximate to nerves that innervate the skin. As is known in the medical art, many nerves that innervate the skin are part of the sympathetic nervous system, which is in turn part of the autonomic nervous system in humans and many animals. Different nerve fibers in the sympathetic nervous system also innervate cardiac tissue as well as other muscles and organs in the body. For example, the sympathetic nervous system is associated with the "fight or flight" response where the sympathetic nervous system activity increases and the pupils dilate, the heart rate increases, bronchioles in the lungs dilate, blood vessels near the surface of the skin constrict, and the sweat glands secrete sweat at a higher rate. The sympathetic nervous system is also associated with the "sympathetic outflow" process that occurs when a subject awakens from sleep. While the sympathetic nervous system includes a large number of nerve bundles that innervate different parts of the body in a subject, the nerves in the sympathetic nervous system are associated with each other and the level of activity in one nerve fiber often corresponds to the level of activity in other nerve fibers in the sympathetic nervous system.

FIG. 1 depicts a monitoring system 100 for monitoring of electrical signals in nerves that are located near the skin. The system 100 includes a plurality of electrodes 104 that are electrically connected to the subject cutaneously or subcutaneously, a signal amplifier and sampler 108, and a signal processor 112. The signal processor 112 includes hardware and software modules that implement a high-pass filter 116 and a nerve activity monitor 120, which identifies and monitors electrical signals in the high-pass filtered signal data that correspond to nerve activity. In the embodiment of FIG. 1, the signal processor 112 implements an optional band-pass filter 140 and electrocardiogram (ECG) monitoring module 140 that identifies and monitors electrical activity in the band-pass filtered signals corresponding to cardiac muscle activity in the subject. The system 100 includes at least one of a visual output device 120, a signal data recording device 124, an alarm 128, an electrical stimulation device, such as a pacemaker, defibrillator, or cardiac resynchronization device 132, or a medicine dispenser device 136.

In the system 100, the electrodes 104 engage the subject in a plurality of locations that enable effective detection of electrical signals from nerves that innervate the skin. In some embodiments, the electrodes are arranged in a configuration for monitoring both the nerve activity and monitoring an ECG. In the system 100, the signal amplifier and sampler 108 is electrically connected to the electrodes 104, including at least one reference electrode and two input signal electrodes. The amplifier and sampler 108 amplifies a differential voltage signal that is received from the electrodes 104, and includes an analog to digital converter (ADC) that generates digitized samples of the amplified signal for further processing by the signal processor 112. In one embodiment, the signal amplifier and sampler 108 is an ML 135 dual-bio amplifier that is manufactured by the ADInstruments of Sydney, Australia. The signal amplifier and sampler 108 is configured to amplify signals in a frequency range of 1 Hz to 5,000 Hz and to generate digital samples of the amplified signals at a rate of 10,000 samples per second.

Figure 14:
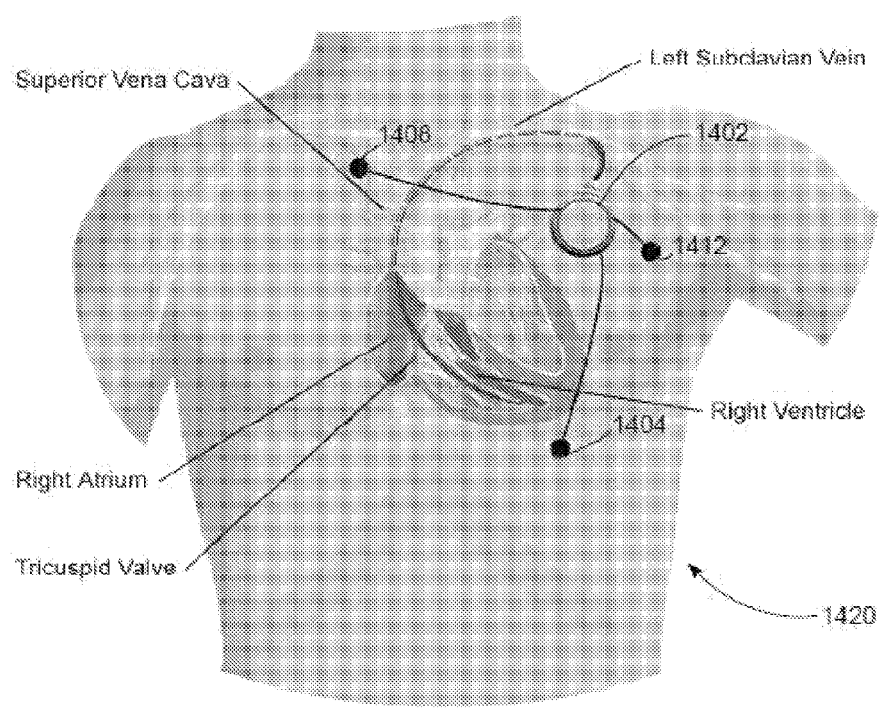
FIG. 14 is an illustration of one embodiment of a system for monitoring nerve activity in a subject including subcutaneous electrodes that are integrated with a pacing or defibrillation device.

FIG. 14 depicts an embodiment with subcutaneous electrodes that are electrically connected to an electronic device that is implanted in a subject. In the embodiment of FIG. 14, all or a portion of the components in the system 100, including the amplifier and sampler 108, are integrated in a pacemaker unit 1402. The pacemaker unit 1402 generates electrical signals to pace the heart in the subject 1420. While FIG. 14 depicts a pacemaker 1402 as an illustrative example of an implanted electronic device, alternative devices include implantable loop recorders, implanted defibrillators, cardiac resynchronization devices, and devices that perform some or all of the functions of an implantable loop recorder, a pacemaker, defibrillator, and cardiac resynchronization device. In the embodiment of FIG. 14, the pacemaker 1402 is electrically connected to three subcutaneous electrodes 1404, 1408, and 1412 in a three-lead configuration. The subcutaneous electrodes 1404, 1408, and 1412 are implanted under the skin of the subject 1420 as part of the implantation procedure for the pacemaker 1402. In FIG. 14, the electrodes 1404-1412 are placed in a configuration for performing three-lead ECG monitoring, with the electrode 1408 being a right-arm lead, the electrode 1412 being a left-arm lead, and the electrode 1404 being a reference lead. While FIG. 14 depicts three electrodes in a three-lead configuration, alternative embodiments include additional electrodes to provide additional differential voltage signals to the pacemaker unit 1402. Additionally, while FIG. 14 depicts electrodes that are connected to the pacemaker unit 1402 through electrical wires, in another embodiment the electrodes 1404-1412 are integrated with the housing of the pacemaker unit 1402.

Figure 15:
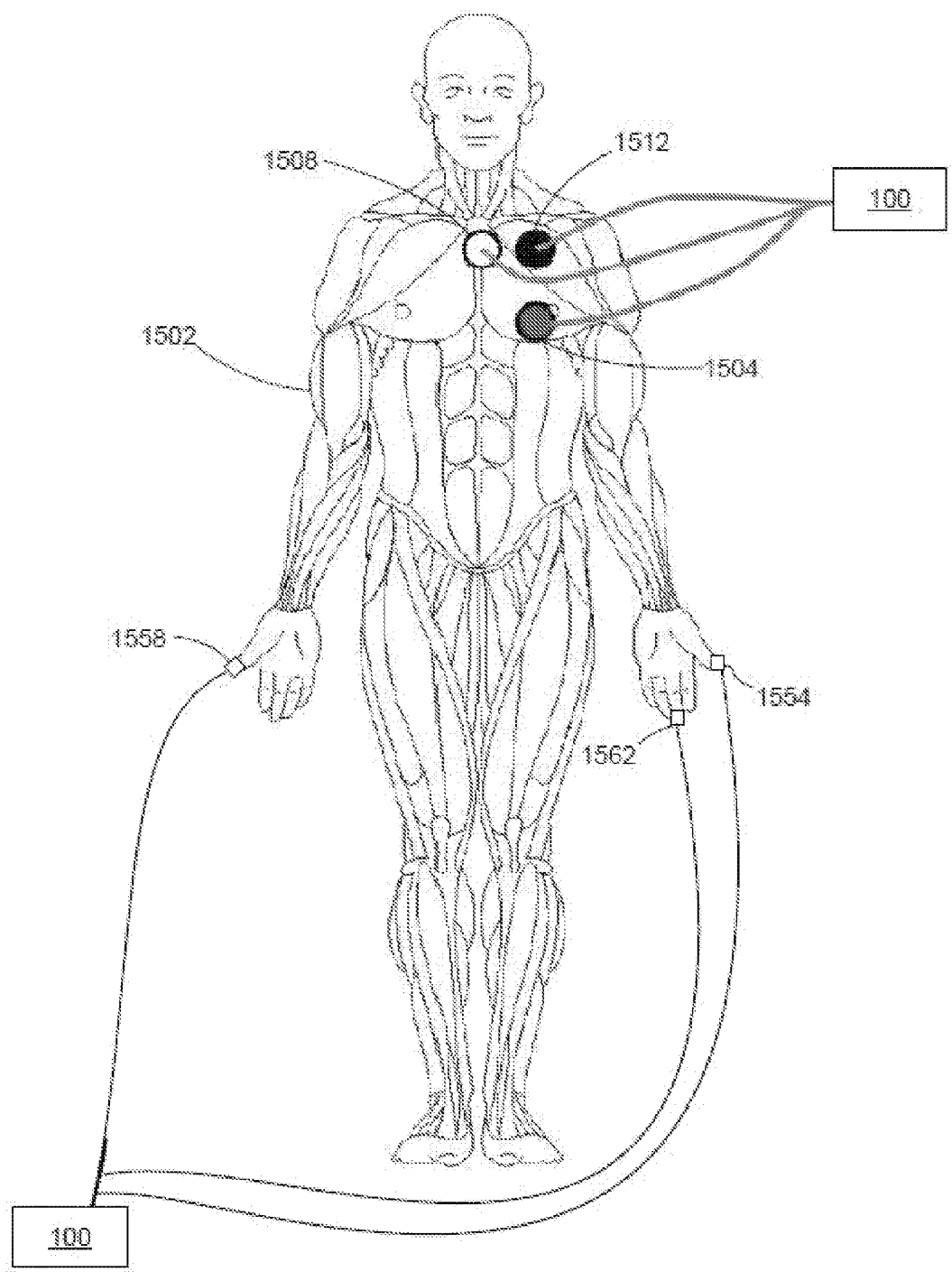
FIG. 15 is an illustration of electrodes that engage the surface of the skin of a subject in a cutaneous configurations for monitoring electrical activity in nerves proximate to the skin of the subject.

In a cutaneous electrode embodiment, electrodes are applied to the surface of the skin of the subject. FIG. 15 depicts two embodiments of cutaneous electrodes that engage the skin of a subject 1502. In FIG. 15, the electrode 1508 is a right-arm lead, the electrode 1512 is a left-arm lead, and the electrode 1504 is a reference lead. In one embodiment, electrodes 1504, 1508, and 1512 engage the surface of the skin of the subject 1502 in a configuration that is used for three-lead ECG monitoring. The leads of the electrodes 1504-1512 are electrically connected to the amplifier and sampler 108 in the system 100. As described below, in addition to monitoring an ECG signal from the subject 1502, the system 100 identifies and monitors nerve activity in nerves that are proximate to the skin in the test subject 1502 in the differential electrical signals from the electrodes 1504-1512. While the embodiment of FIG. 15 depicts the electrical leads 1504-1512 in a three-lead configuration, an alternative embodiment includes electrical leads that engage the skin of the subject 1502 in a twelve-lead configuration that is known to the art for monitoring ECG signals.

While the electrode configurations depicted above in FIG. 14 and FIG. 15 show electrode configurations that are suitable for monitoring both the ECG and the nerve activity in nerves that are proximate to the skin of the subject. In an alternative arrangement, the electrodes monitor the electrical activity in nerves that innervate the skin but are not necessarily configured to monitor the ECG. For example, in FIG. 15 electrodes 1554 and 1562 engage the skin on the digits on the left hand of the subject 1502 and an electrode 1558 engages the skin on a digit on the right-hand of the subject 1502. The electrodes 1554-1562 are electrically connected to the amplifier and sampler 108 in the monitoring system 100. The electrodes 1554-1562 are easily attached and removed from the subject 1502 for monitoring of the electrical activity in the nerves that innervate the skin around the digits on both the right and left hands. In some situations, the subject 1502 attaches and remove the electrodes 1554-1562 without requiring additional assistance from a medical professional to enable monitoring of nerve activity when the subject 1502 is outside of a medical facility.

Referring again to FIG. 1, the signal processor 112 in the system 100 is a digital logic device that performs signal processing to identify nerve activity in data samples that are received from the signal amplifier and sampler 108. In one embodiment, the signal processor 112 is implemented using a mobile electronic device, such as a smartphone or tablet, a personal computer (PC), or any suitable computing device that includes a central processing unit (CPU) with one or more cores and a graphical processing unit (GPU). The CPU and optionally the GPU execute stored software instructions to apply filters the samples and to perform other signal processing functions on the data samples. The GPU also generates a graphical display of the signal data using a visual output device 120, such as an LCD display. One embodiment of software that can be configured for the signal processing tasks in the signal processor 112 is the PowerLab data acquisition software that is sold commercially by ADInstruments of Sydney, Australia. In an alternative embodiment, the signal processor 112 is implemented using one or more digital logic devices including application specific integrated circuits (ASICs), field programmable gate arrays (FPGAs), and digital signal processor (DSP) devices. In an embodiment where the signal processor 112 is a part of an implanted electronic device, such as the pacemaker 1402 in FIG. 14, the signal processor 112 is implemented using low-power digital logic devices to enable long-term operation between either replacement or recharging of a battery that powers the implanted electronic device.

The signal processor 112 identifies and monitors the electrical signals corresponding to nerve activity in the subject by application of the high-pass filter 116 to the samples that are received from the signal amplifier and sampler 108. As depicted in more detail below, the electrical activity in the nerves that innervate the skin occurs at higher frequencies and lower amplitudes than the electrical signals generated in the cardiac muscle during a heartbeat. In the embodiment of FIG. 1, the lower 3 dB cutoff frequency of the high-pass filter 116 is adjustable in a range of approximately 100-150 Hz in order to attenuate the lower-frequency signals from the heart muscle that are typically recorded in an electrocardiogram. The electrical activity corresponding to the nerves occurs in a range of hundreds of hertz up to several kilohertz, and the high-pass filter 116 provides the higher frequency signals to the nerve activity monitor module 120 while attenuating the lower-frequency signals that correspond to cardiac muscle activity and electrical signals from other muscles in the subject. Prior art electrocardiogram systems apply a low-pass or band-pass filter to the high-frequency components of measured signals are discarded as noise, but the monitoring system 100 monitors a range of frequencies that are well above the frequencies of interest to electrocardiogram monitoring to identify the electrical signals corresponding to the nerve activity.

In the configuration of FIG. 1, the signal processor 112 includes an optional band pass filter 140 and ECG monitoring module 144 to enable the signal processor 112 to monitor the ECG of the subject using the amplified signal samples from the signal amplifier and sampler 108. In one embodiment, the band-pass filter 140 has a lower cutoff frequency of approximately 0.5 Hz and an upper cutoff frequency of approximately 100 Hz. In embodiments where an alternating current (AC) electrical signal is used to supply power to one or more components in the monitoring system 100, the band-pass filter 140 also includes a notch-filter that attenuates frequencies near the primary frequency of the AC signal, such as 50 Hz or 60 Hz.

In addition to monitoring the electrical signals that correspond to the nerve activity and optionally the ECG, the signal processor 112 is configured to analyze the signals to identify changes in the level of nerve activity and take an appropriate action in response to changes in the nerve activity. For example, in one configuration the signal processor 112 identifies a baseline of the nerve activity over time including an average amplitude and variation of the electrical signals that correspond to the nerve activity. In one configuration, the signal processor 112 generates an output of the nerve activity and optionally the ECG with the visual output device 120, and stores data corresponding to the recorded signals in the signal data recording device 124, which is typically a digital data storage device such as a solid-state or magnetic disk. The signal processor 112 generates an alert signal or activates a medical device in response to a rapid increase or decrease in the level of electrical activity from the baseline. In the embodiment of FIG. 1, the signal processor 112 is also configured to identify a baseline in the electrocardiogram of the subject, and the signal processor 112 generates the output signal in response to deviations from the respective baselines in one or both of the nerve activity and the ECG activity.

Figure 2:
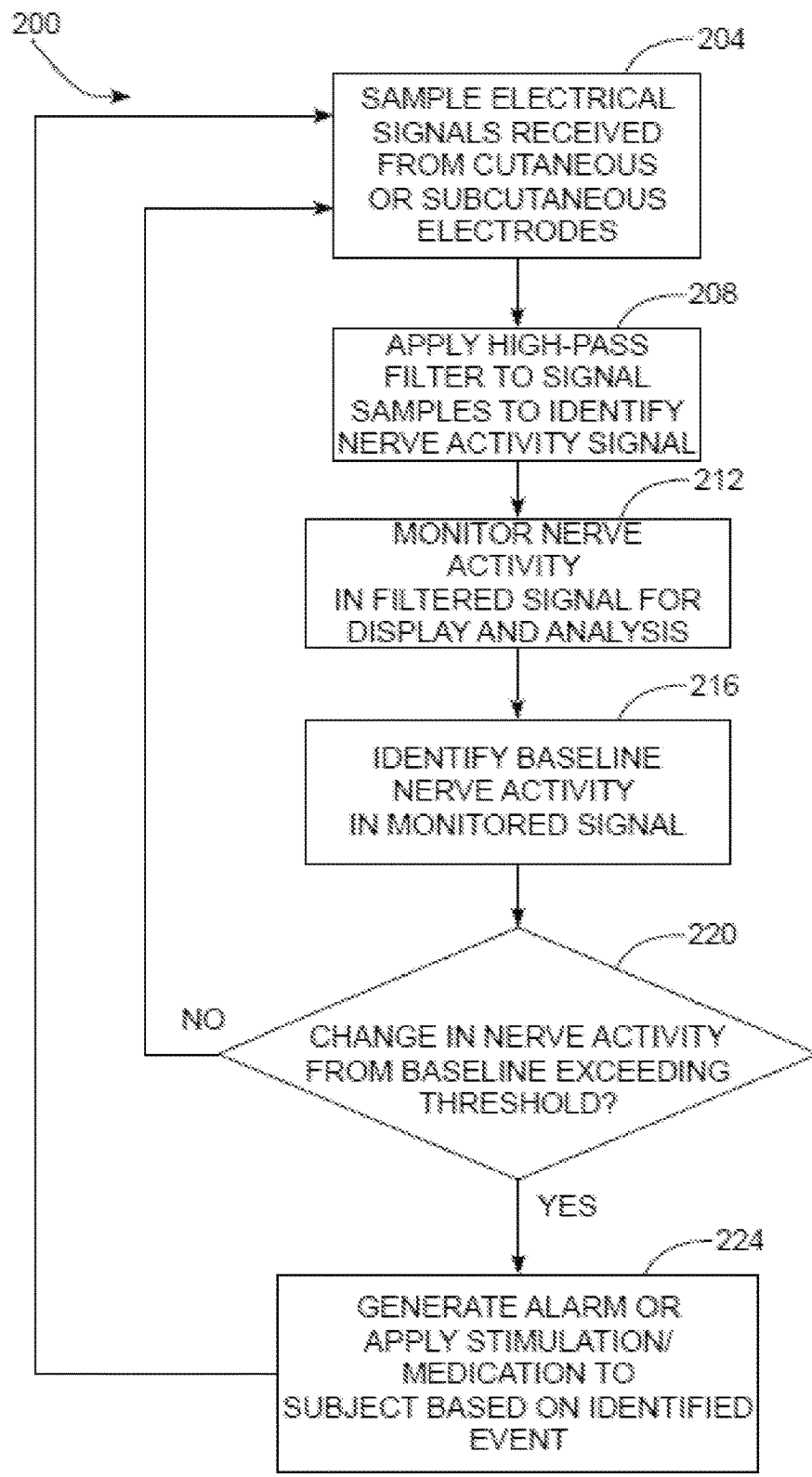
FIG. 2 is a block diagram of a process for monitoring electrical activity in nerves that are near the surface of the skin in a subject.

FIG. 2 depicts a process 200 for operation of a monitoring system to monitor nerve activity in a subject using cutaneous or subcutaneous electrodes that record electrical activity in nerves that innervate the skin. In the discussion below, a reference to an action or function of a component in a monitoring system performed by the process 300 refers to one or more programmed instructions being executed by a processor or controller to carry out the action or function in conjunction with components in the monitoring system. FIG. 2 is described with reference to the monitoring system of FIG. 1 for illustrative purposes.

Process 200 begins as the monitoring system samples electrical signals that are received via cutaneous or subcutaneous electrodes (block 204). As described above, three or more electrodes are placed on the skin of the subject in a cutaneous configuration or are implanted under the skin of the subject in a subcutaneous configuration. In the system 100, the amplifier and sampler 108 amplifies the differential voltage signals that are received from the electrodes and generates digitized samples of the signals.

Process 200 continues with application of a high-pass filter to the signal samples (block 208). In the system 100, the high-pass filter 116 has a lower cutoff frequency in a range of 100 Hz to 150 Hz to attenuate lower-frequency electrical signals that correspond to cardiac activity in the subject instead of the nerve activity. The lower-frequency cutoff of the high-pass filter can be adjusted based on the characteristics of different subjects to enable identification of the electrical signals in the nerves that innervate the skin while attenuating the electrical signals from muscles and other sources of electrical noise in the subject.

Process 200 monitors the high-frequency signals that pass through the high-pass filter to enable a doctor or other healthcare professional to monitor the nerve activity in the subject (block 212). In the system 100, the visual output device 120 displays a graph of the electrical signals that correspond to the nerve activity. Examples of visual displays of electrical signals corresponding to the nerve activity are described below in FIG. 4-FIG. 12. The monitoring system 100 also records the data in the signal data recording memory 124 for later analysis by doctors and healthcare professionals. In one configuration, the monitoring system 100 is configured to record and display the electrical signals corresponding to the nerve activity, and a doctor or other healthcare professional observes the monitored data during the course of medical treatment for a subject.

In one embodiment of the process 200, the monitoring system 100 is configured in a passive operating mode to display the nerve activity on the display device 120 and to record the nerve activity in the memory 124 for analysis by medical professionals. In the passive operating mode, the monitoring system 100 does not activate therapeutic devices or deliver medicine in an automated manner, although a doctor or other healthcare provider reviews the graphs of nerve activity as part of diagnosis and treatment in a patient. The passive operating mode can be used, for example, during diagnosis of a medical condition, during long-term monitoring of a patient to assess progress in a course of medical treatment, and for studies of subjects during clinical trials or other scientific research.

In some embodiments of process 200, the monitoring system analyzes the electrical activity in the nerves that innervate the skin to generate a baseline measurement of nerve activity in the subject (block 216). As described above, in human subjects and many animal subjects, the skin is innervated with many nerves that are part of the sympathetic nervous system. The baseline activity monitoring indicates the level of sympathetic nerve activity in the subject over time, including an average amplitude and expected variation of the activity in the sympathetic nerves near the skin. If the identified nerve activity remains within a predetermined threshold of the baseline (block 220), then process 200 continues to sample additional signals and monitor the nerve activity in the subject as described above with reference to the processing of blocks 204-216.

During process 200, if the monitoring system identifies a rapid change in the electrical signals corresponding to the sympathetic nerve activity that deviates from the baseline by more than a predetermined threshold (block 220), then the monitoring system generates an alarm or takes another action in response to the identified change in nerve activity (block 224). In the monitoring system 100, the alarm 128 is a visible or audible alarm that notifies the subject or a healthcare professional of the identified change in the nerve activity. In another embodiment, the alarm 128 is configured to send a message, such as a page, email, or text message, through a data network to alert a remote healthcare professional of the identified event. In another embodiment, the alarm signal triggers the implanted electrical stimulation device 132 or medicine delivery device 136. In still another embodiment, the alarm 128 generates a message that is stored in the signal data recording memory 124 for later analysis. As described below, changes in the nerve activity can correspond to different medical events, including cardiac arrhythmias. Additionally, in some instances the change in the nerve activity occurs prior to onset of the symptoms of the medical event, and the alarm 128 enables prompt action if a medical event that occurs or will occur in the subject requires action by a medical professional.

During process 200, the electrical activity in the nerves that innervate the skin correspond to multiple events that occur in the subject. For example, many cardiac arrhythmias are preceded by rapid changes in the level of sympathetic nerve activity and the level of sympathetic nerve activity often remains abnormally high or low during an episode of cardiac arrhythmia. Thus, the nerve activity that is identified and monitored during process 200 is also referred to as a "NeuroElectrocardiogram" (NECG or neuECG) because the electrical signals identified in the neurons that innervate the skin provide information about the activity in the heart. In the process 200, the monitoring system 100 is configured to identify changes in heart activity using only the NECG signal, while in another configuration described below, the monitoring system 100 identifies changes in the heart activity using both the NECG and a traditional ECG signal.

The cardiac activity of the subject is not the only type of medical event that corresponds to changes in the nerve activity in the sympathetic nervous system. Other changes in the level of nerve activity in the subject can correspond to the onset of symptoms related to various other medical conditions including, but not limited to, hyperhidrosis (sweaty palms), paralysis, stroke, diabetes, seizure disorder, syncope, disturbance of consciousness, hyperthyroidism, hypertension and neuromuscular diseases. Other areas of treatment include biofeedback monitoring performed by neurologists to control neuropsychiatric disorders. In such approaches, the monitoring system 100 may be used to identify a suitability of a patient to receive a therapy aimed at modifying an identified nerve activity for treatment of certain medical conditions or diseases, such as hypertension and cardiac arrhythmia. For example, a neuromodulation therapy, such as renal sympathetic denervation, may be performed to reduce or modify sympathetic nerve activity. Monitored nerve activity may also be desirable for providing guidance while performing a procedure, and also for determining an effectiveness of a treatment after delivery with reference to a difference in the identified nerve activity. Additionally, another area includes lie-detection tests, because the sympathetic nerve activation is the mechanism that regulates sweating, pupil contraction, and other physiological responses that are measured during lie detector tests. Thus, the monitoring system 100 identifies changes in the nerve activity of the subject that correspond to changes in cardiac activity and the onset of symptoms in different diseases and conditions that affect the subject.

As described above, in one configuration of the monitoring system 100, an optional medication delivery device 132 is implanted in the subject or otherwise incorporated into the monitoring system 100 to deliver a medicine to the subject. As used herein, the term "medicine" is defined broadly to include any chemical that is used for treatment of a medical condition in a subject. For example, one type of medicine delivery device is an insulin pump that is implanted or carried by the subject. In one configuration, the NECG signals in the subject correspond to a hypoglycemic condition in the subject. As is known in the art, patients with hypoglycemia may develop autonomic activation, which corresponds to activity in the autonomic nervous system that presents as hunger, trembling of hands or legs, palpitations, anxiety, pallor, sweating in the subject. The autonomic activation includes abnormal electrical activity in the autonomic nerves, including nerves that innervate the skin. Thus, the NECG signal that monitors abnormal nerve activity can be used to identify clinical conditions that require an adjustment to the level of insulin infusion in the insulin pump.

Figure 3:
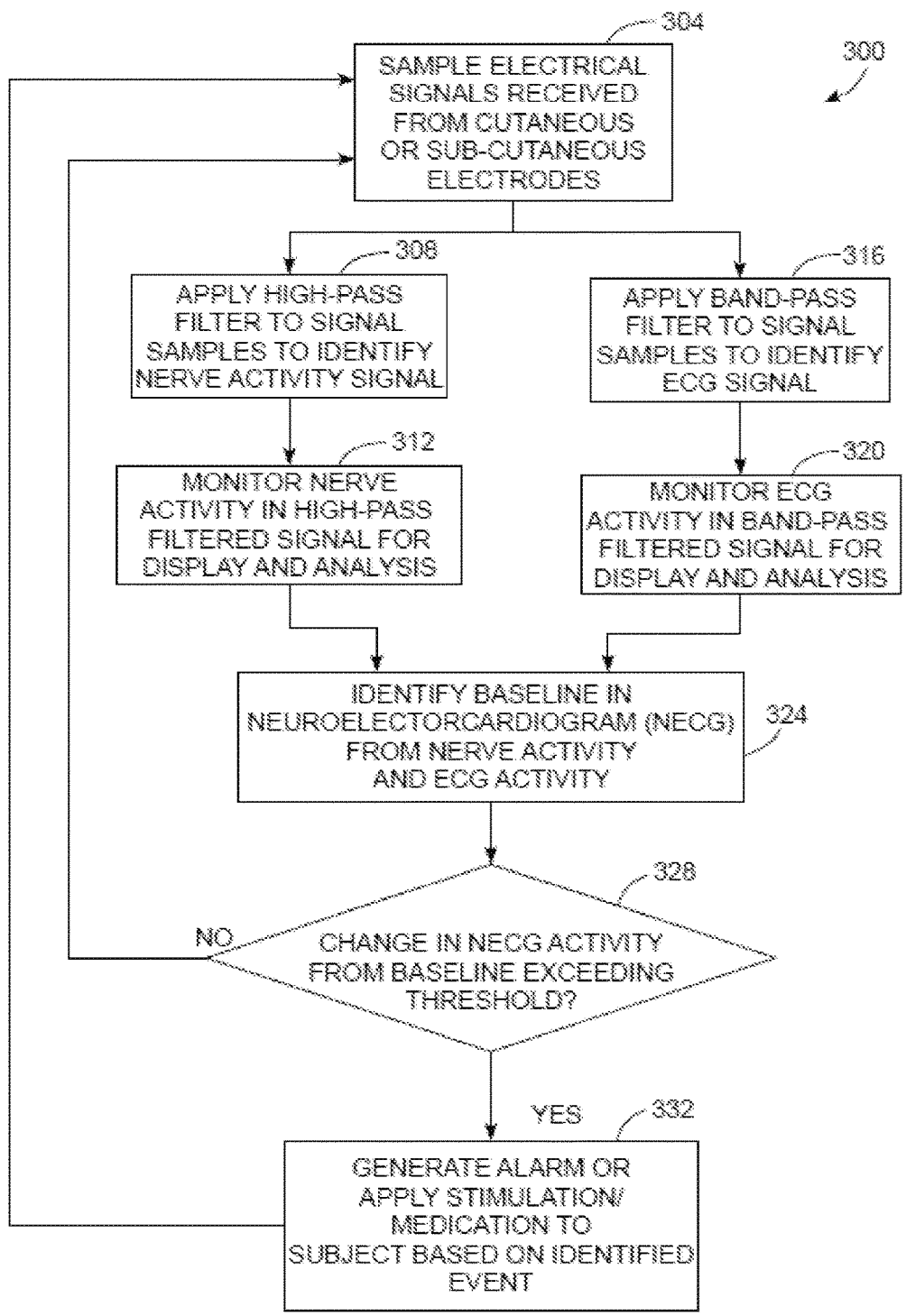
FIG. 3 is a block diagram of a process for monitoring electrical activity in nerves that are near the surface of the skin in a human subject in conjunction with monitoring an electrocardiogram (ECG) in the subject.

FIG. 3 depicts a process 300 for operation of a monitoring system to monitor nerve activity in a subject using cutaneous or subcutaneous electrodes that record electrical activity in nerves that innervate the skin as well as record electrical signals corresponding to an electrocardiogram in the subject. In the discussion below, a reference to an action or function of a component in a monitoring system performed by the process 300 refers one or more programmed instructions being executed by a processor or controller to carry out the action or function in conjunction with components in the monitoring system. FIG. 3 is described with reference to the monitoring system of FIG. 1 for illustrative purposes.

Process 300 begins in the same manner as process 200 as the monitoring system samples electrical signals that are received via cutaneous or subcutaneous electrodes (block 304). During process 300, the monitoring system supplies the signal samples to a high-pass filter to identify nerve signal activity (block 308) and to monitor the NECG nerve activity in the high-pass filtered signal (block 312) in a similar manner to the filtering and monitoring that are described above with reference to the processing of blocks 204 and 208, respectively, in the process 200. Process 300 monitors both the NECG activity from the nerves that innervate the skin and in the electrocardiogram from cardiac muscle during heartbeats, and identifies changes in cardiac activity based on both the NECG and the ECG.

Process 300 includes concurrent monitoring of both the electrocardiogram (ECG) and nerve activity in the electrical signals that are received from the subject. In addition to identifying and monitoring nerve activity in the signal samples, the monitoring system 100 applies a band-pass filter to the signal samples to identify the ECG signal (block 316). In the monitoring system 100, the signal processor 112 applies the band-pass filter 140 to the signal samples to identify the portion of the signals that correspond to the ECG activity in the subject. For example, the signal processor applies a band-pass filter to attenuate signals below 0.5 Hz, such as a DC offset voltage, and to attenuate the high-frequency signals that are above 100 Hz. In the embodiment of FIG. 1, the signal processor 112 receives the signals from the electrodes 104 in the form of digitized samples. The signal processor 112 applies the high-pass filter 116 and low-pass filter 140 to separate copies of the digital sample data to enable concurrent filtering and monitoring of both the nerve activity signals and the ECG signals. In an alternative embodiment that includes analog filters for the high-pass and band-pass filtering, the amplified electrical signals from the electrodes are split into two substantially identical signal waveforms with one waveform being passed through the high-pass filter and the other waveform being passed through the band-pass filter.

During process 300, the monitoring system 100 monitors the activity in the ECG using the band-pass filtered signals (block 320). In one embodiment, the signal processor 112 monitors the ECG signals using one or more known monitoring techniques to identify the heart rate and other information about the activity of the heart in the subject from, for example, the QRS complexes in one or more heartbeats that are identified in the ECG signal. In one configuration of the monitoring system 100, the signal processor 112 displays traces of both the nerve activity and the ECG in tandem on the visual output device 120 to enable a doctor or other healthcare professional to view the ECG activity and nerve activity simultaneously. As depicted below, the amplitude of the ECG signal is typically greater than the amplitude of the nerve activity signals, and the signal processor 112 scales the signals appropriately to produce visual output graphs that clearly depict both the nerve activity and the ECG activity. In the monitoring system 100, the signal processor 112 also stores both the NECG and ECG data in the signal data recording device 124 for further analysis by a doctor or healthcare professional.

In one embodiment of the process 300, the monitoring system 100 is configured in a passive operating mode to display both the NECG nerve activity and the ECG activity on the display device 120 and to record the NECG and ECG activity in the memory 124 for analysis by medical professionals. In the passive operating mode, the monitoring system 100 does not activate therapeutic devices or deliver medicine in an automated manner, although a doctor or other healthcare provider reviews the graphs of nerve activity as part of diagnosis and treatment in a patient. In the passive operating mode associated with the process 300, doctors or healthcare providers review the NECG and the ECG in tandem to identify changes in the heart activity and to diagnose heart conditions. The NECG data provide additional information about the nerve activity in the patient that complement and expand on the information provided by traditional ECG monitoring. The passive operating mode can be used, for example, during diagnosis of a medical condition, during long-term monitoring of a patient to assess progress in a course of medical treatment, and for studies of subjects during clinical trials or other scientific research.

In some embodiments, process 300 continues as the monitoring system identifies a baseline of activity in the subject using both the data from the monitored NECG activity and the data from the ECG activity (block 324). The baseline for both the NECG and ECG activity includes average levels of activity in both the nerves that innervate the skin and generate normal activity in the heart of the subject. For example, the NECG baseline includes the average amplitude and expected variation in the sympathetic nerves for the subject, while the ECG baseline includes an average heart rate and an expected variation in times between heart beats. If the monitoring system identifies NECG and ECG signals that are both within a predetermined threshold of the expected baseline activity in the subject (block 328) then process 300 continues to sample additional signals and monitor the NECG and ECG activity in the subject as described above with reference to the processing of blocks 304-324.

During process 300, if either or both of the NECG and ECG activity deviate from the baseline by greater than the predetermined threshold (block 328), then the signal processor 112 in the monitoring system 100 generates a signal to activate the alarm 128, activate the electrical stimulation device 132, or deliver medicine with the medicine delivery device 136 (block 332). For example, as depicted below, a rapid increase in the amplitude of the NECG signal can occur prior to and during an episode of cardiac arrhythmia. In one configuration the signal processor 112 activates the alarm 128 to alert a doctor or other healthcare professional to the onset of a cardiac arrhythmia. In human patients that are at risk of sudden heart failure, an advanced warning of even a few seconds prior to the onset of heart failure can assist doctors in resuscitating a patient. In an embodiment where the monitoring system 100 includes the implanted electrical stimulator, the signal processor 112 activates the electrical stimulator to, for example, pace the heart to counteract the arrhythmia.

Both the processes 200 and 300 can be used for continuous recording of nerve activity over prolonged period of time, such as a 24 to 72 hour monitoring period. In one embodiment, the monitoring system 100 integrates the identified NECG signals over time and displays a summary of the nerve activity on an hour by hour basis for analysis by a doctor or healthcare professional. In one configuration, the signal processor 112 integrates the signals on an hourly basis to identify a total magnitude of nerve activity during each hour of the monitoring process. The signal processor 112 optionally integrates the ECG activity to identify, for example, an average heart rate or variance in heart rate during each hour. The data may be useful for arrhythmia risk stratification. For example, sudden cardiac death and atrial fibrillation both tend to occur more often in the morning than in the afternoon. This is known as circadian variation, which is attributed to the heightened autonomic tone in the morning. Detecting and analyzing the circadian variation of the nerve activity may help predict the arrhythmic risk. Medical or surgical intervention may be triggered by the nerve activities to prevent sudden death or arrhythmia in patients with abnormal patterns of ambulatory autonomic nerve activities over a prolonged period of time.

As described above, the level of nerve activity that is identified in nerves that innervate the skin of a subject can change rapidly prior to and during the onset of cardiac arrhythmias. FIG. 4-FIG. 9 depict ECG and NECG data that were recorded from a human subject and displayed for analysis. In each of FIG. 4-FIG. 9, the first graph is generated by an electrode surgically implanted in the epicardial fat pad of a patient undergoing open heart surgery. The other end of the electrode is exteriorized and connected to the recording system. (The electrode we used during this study is the standard electrode commonly used for postoperative pacing. This temporary pacing electrode is removed 3 days after surgery by simply pulling the electrode out of the skin.) The second graph is recorded by electrodes non-invasively placed on the skin. The recordings of the first and second graphs are produced simultaneously, and the second graph depicts electrical activity corresponding to both the ECG signal from the heart and nerve activity in the autonomic nerves that innervate the skin. As depicted in more detail below, the amplitude of the ECG signal is much greater than the amplitude of the nerve signals, so the second set of graphs effectively depict the ECG in the subject. Both first and second graphs were sampled at very high rate (10,000 samples per second) and with amplifiers that can record a wide frequency range. A third graph (the NECG graph) is generated from the second graph using a high-pass filter and signal processor as depicted above in FIG. 1 to isolate the NECG signal from the ECG signal and to monitor the NECG signal.

Figure 4:
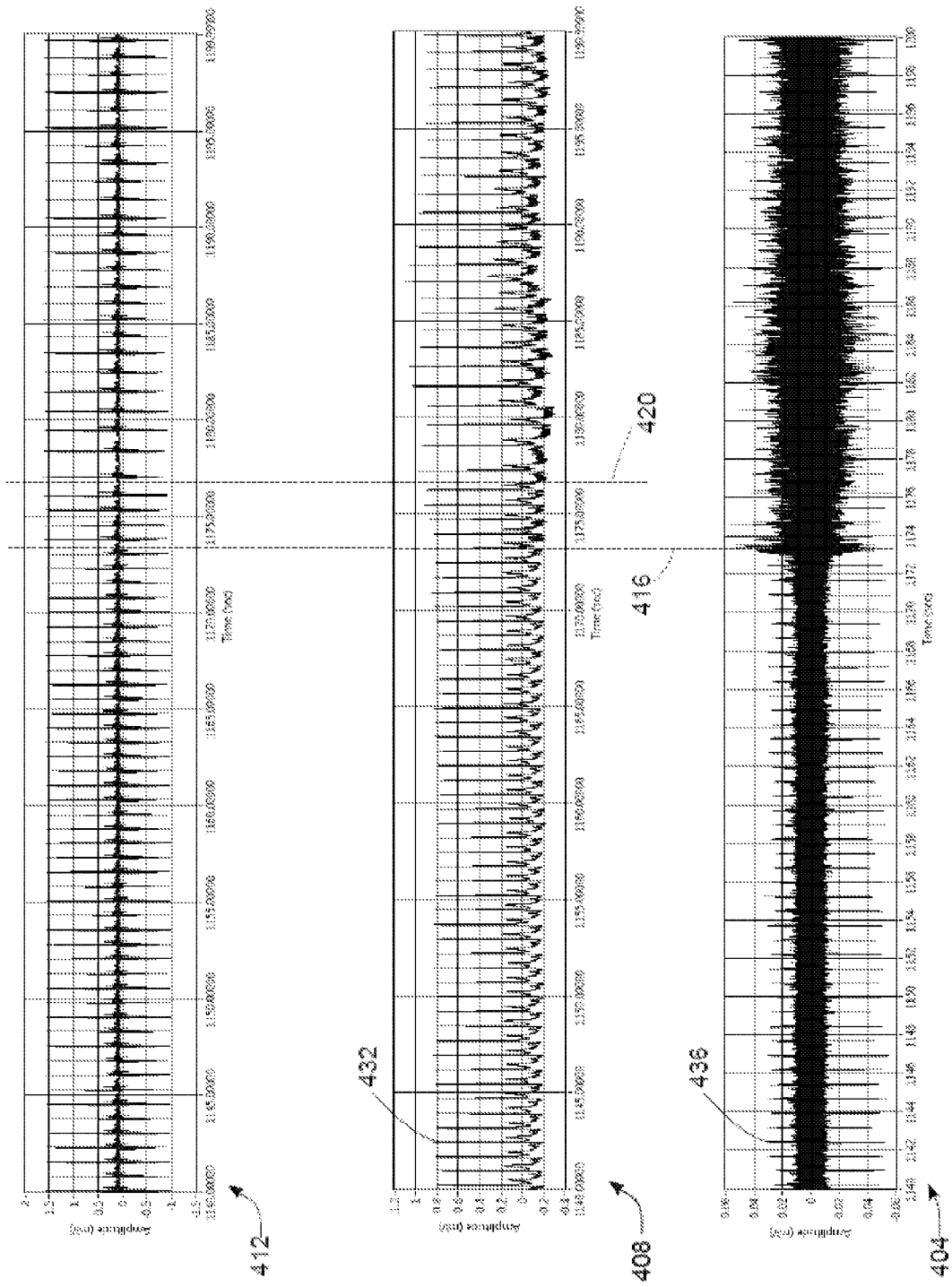
FIG. 4 is a set of graphs recorded by electrodes on the skin of a human subject, depicting a relationship between electrical activity in nerves that are near the skin of a subject and cardiac activity in the subject before and during an episode of bradycardia.

FIG. 4 depicts an NECG graph 404 and ECG graph 408 that correspond to signals that are measured from electrodes placed on the skin of the human subject. The graph 412 depicts a measurement of electrical activity taken from fat pads on the heart of the human subject using implanted electrodes. Each of the graphs depicts an amplitude of measured signals in millivolts over time. As depicted in FIG. 4, the measured amplitude of the ECG from the electrodes on the skin of the subject in the graph 408 is approximately 1 millivolt, while the measured amplitude of the NECG activity in graph 404 varies between approximately 0.06 millivolts during a period of NECG activity in a baseline measurement before time index 416 to approximately 0.12 millivolts during a period of heightened NECG activity occurring after the time index 416. The amplitude of the ECG signal is similarly larger than the amplitude of the NECG signal in FIG. 5-FIG. 9.

In FIG. 4, the NECG activity graph 404 indicates an increase in NECG electrical activity at the time index 416. The external and internal ECG graphs indicate an onset of bradycardia (slowing of the heart rate) at time index 420, which is approximately three seconds after the initial increase in NECG electrical activity. In FIG. 4, the increased level of NECG activity in the graph 404 continues during an episode of bradycardia that is depicted as a reduced heart rate in the subject in the graphs 408 and 412. Thus, in the example of FIG. 4, the NECG signal depicted in the graph 404 indicates the onset of an arrhythmia in the heart of the human subject before the arrhythmia is apparent in the ECG graphs 408 and 412.

Each of the NECG graphs depicted in FIG. 4-FIG. 9 is generated from signals that are passed through a high-pass filter, such as the high-pass filter 116 in the signal processor 112 in FIG. 1. While the NECG signal graphs remove some portions of the ECG signal, the spikes in the ECG signals that correspond to the R-wave in the QRS complex in the ECG are also present in the filtered NECG data. For example, the R-wave spike 432 in the ECG graph 408 occurs at the same time as a spike 436 in the NECG graph 404. As described above, in some monitoring configurations, the monitoring system 100 only monitors the NECG signal and can identify some characteristics of the standard ECG signal, such as the heart rate, using features of the NECG signal alone.

Figure 5:
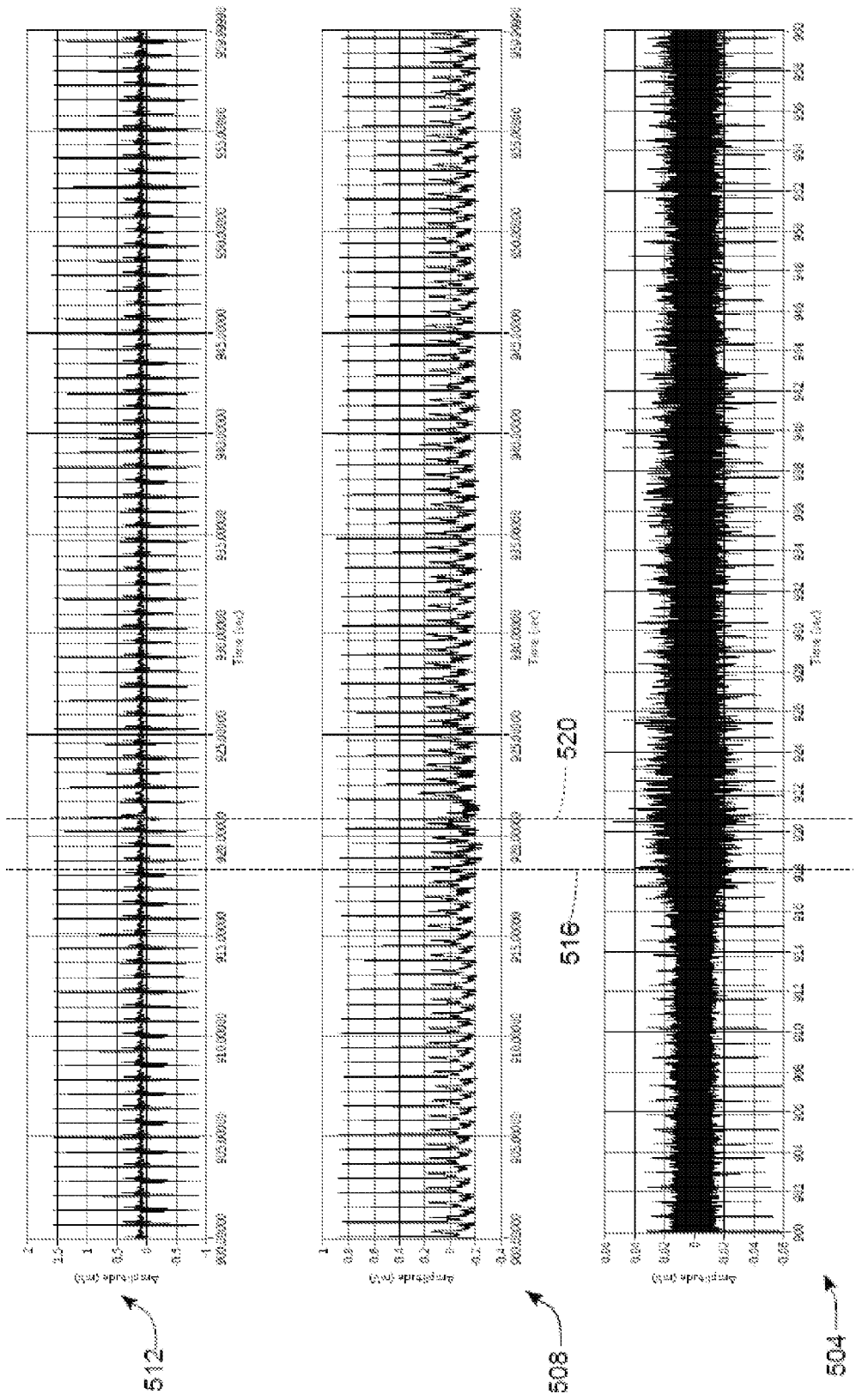
FIG. 5 is a set of graphs recorded by electrodes on the skin of a human subject, depicting a relationship between electrical activity in nerves that are near the skin of a human subject and cardiac activity in the subject before and during an episode of tachycardia.

FIG. 5 depicts NECG graph 504 and ECG graph 508 taken from electrodes on the skin of the subject, and ECG graph 512 taken from the internally implanted electrodes. In FIG. 5, an increase in NECG activity at time index 516 occurs approximately three seconds before the onset of premature contractions in the heart of the subject. The premature contractions are indicated in the ECG signals 508 and 512 beginning at time index 520. The NECG graph 504 indicates an elevated level of activity in the nerves near the skin of the subject continuing during the episode of premature muscle contraction in the subject.

Figure 6:
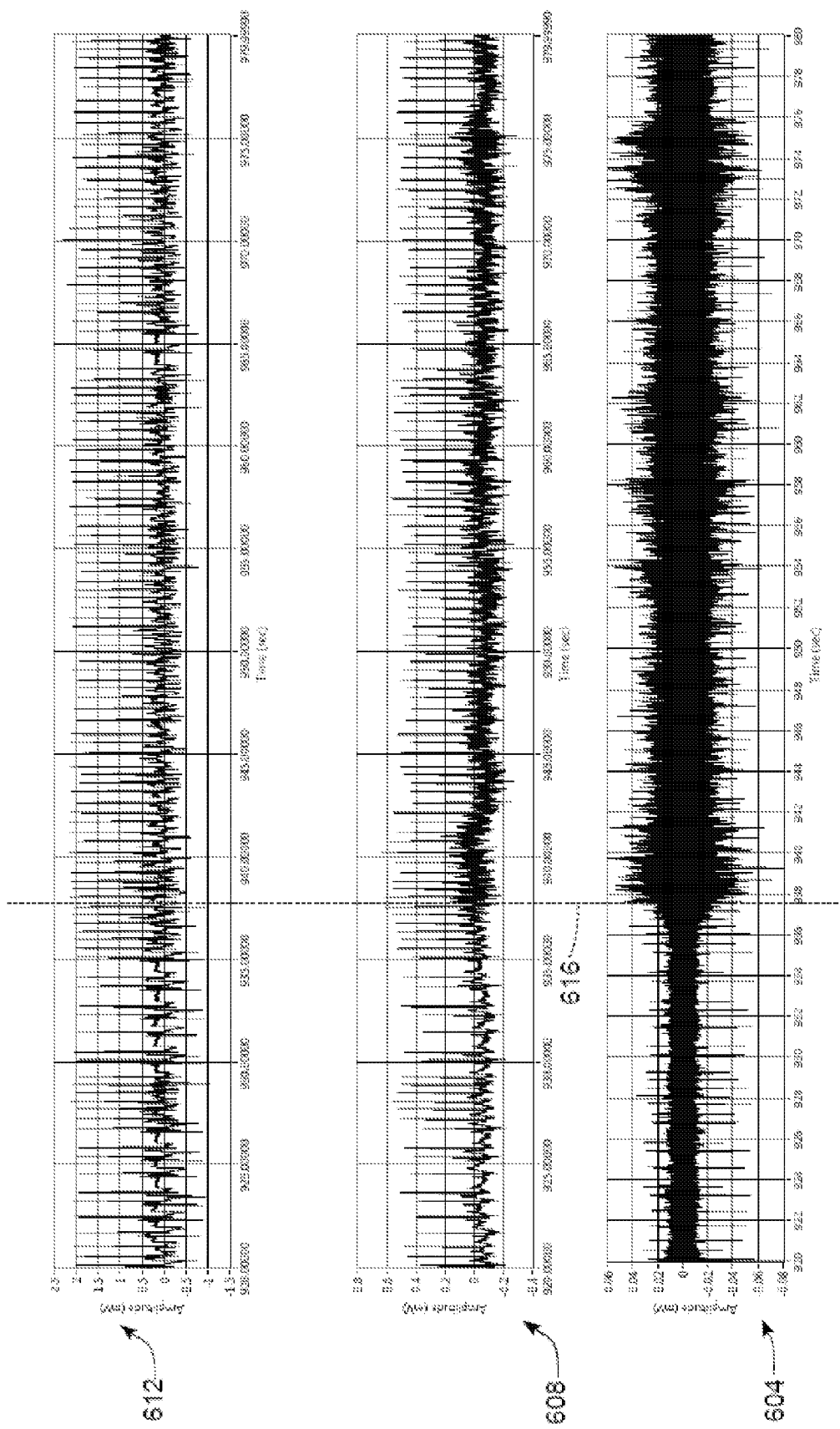
FIG. 6 is a set of graphs recorded by electrodes on the skin of a human subject, depicting a relationship between electrical activity in nerves that are near the skin of a human subject and cardiac activity in the subject before and during an episode of premature contraction in the heart muscle.

FIG. 6 depicts NECG graph 604 and ECG graph 608 taken from electrodes on the skin of the subject, and ECG graph 612 taken from the internally implanted electrodes. In FIG. 6, an increase in NECG activity at time index 616 occurs during the onset of tachycardia (increased and irregular heart rate) in the subject. The ECG graphs 508 and 512 also indicate the episode of tachycardia. The NECG graph 504 indicates an elevated level of activity in the nerves near the skin of the subject continuing during the episode of tachycardia in the subject.

Figure 7:
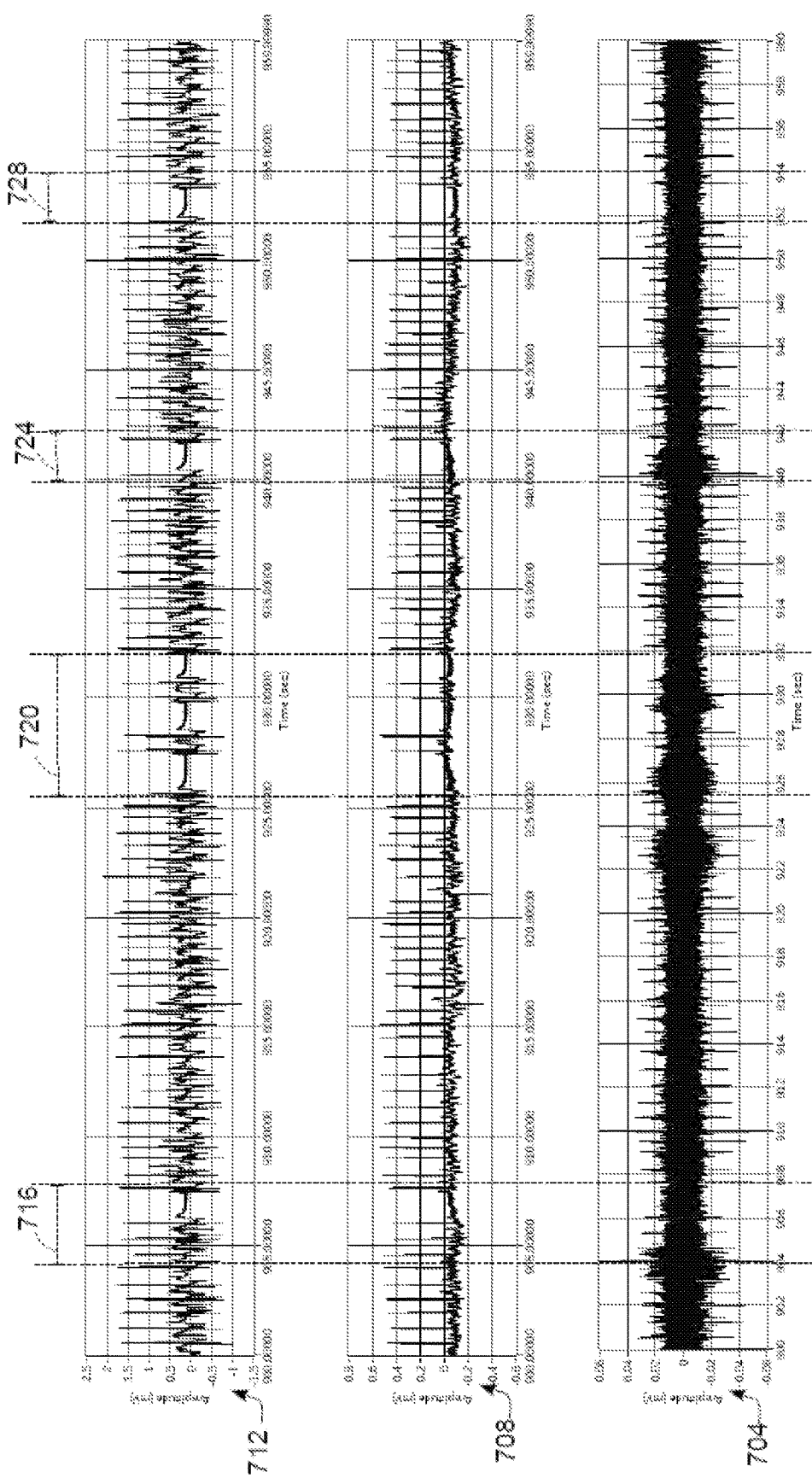
FIG. 7 is a set of graphs recorded by electrodes on the skin of a human subject, depicting a relationship between electrical activity in nerves that are near the skin of a human subject and cardiac activity in the subject between episodes of intermittent arrhythmia in the heart.
Figure 8:
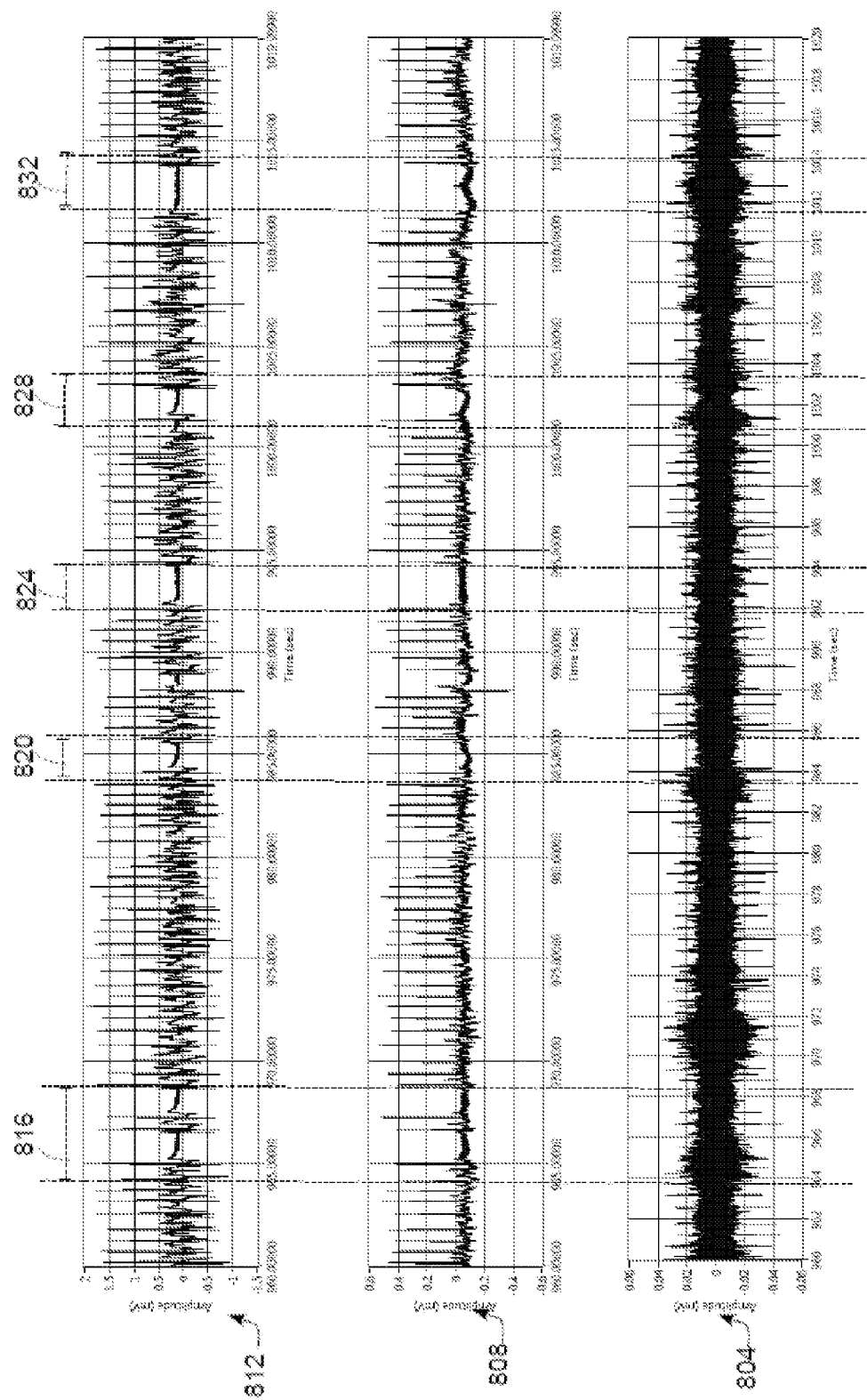
FIG. 8 is another set of graphs recorded by electrodes on the skin of a human subject, depicting a relationship between electrical activity in nerves that are near the skin of a human subject and cardiac activity in the subject between episodes of intermittent arrhythmia in the heart.
Figure 9:
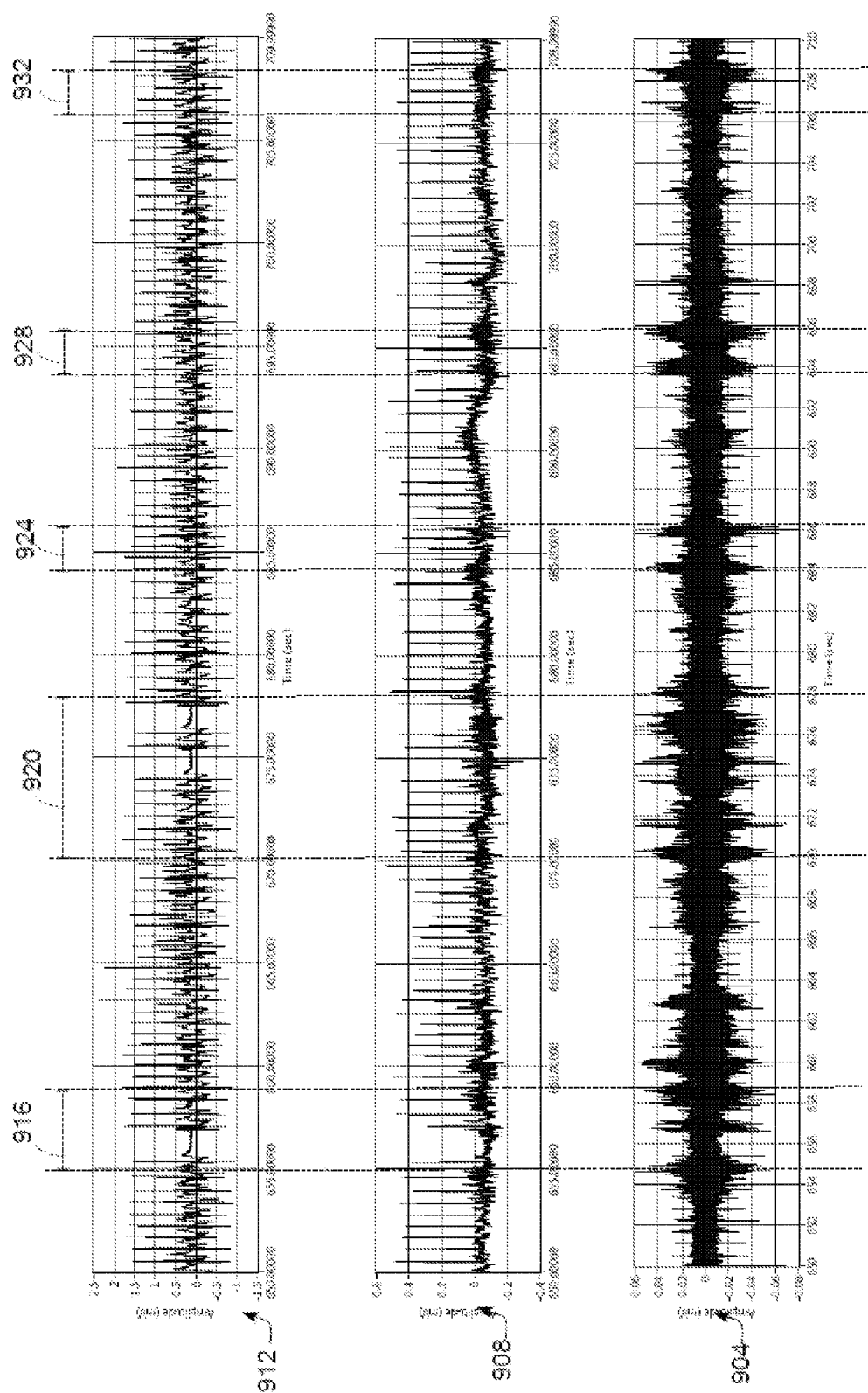
FIG. 9 is another set of graphs recorded by electrodes on the skin of a human subject, depicting a relationship between electrical activity in nerves that are near the skin of a human subject and cardiac activity in the subject between episodes of intermittent arrhythmia in the heart.

FIG. 7-FIG. 9 each depict intermittent bursts of electrical activity in the NECG graphs 704, 804, and 904 in FIG. 7, FIG. 8, and FIG. 9, respectively. In FIG. 7, fluctuations in the amplitude of the NECG activity in graph 704 occur before and during intermittent periods of heart arrhythmia that are depicted in the surface ECG graph 708 and implanted ECG graph 712 in regions 716, 720, 724, and 728. FIG. 8 depicts similar periods of arrhythmia in regions 816, 820, 824, 828, and 832 in the NECG graph 804, surface ECG graph 808, and implanted ECG graph 812. FIG. 9 also depicts periods of intermittent arrhythmia in regions 916, 920, 924, 928, and 932 in the NECG graph 904, surface ECG graph 908, and implanted ECG graph 912.

Figure 10:
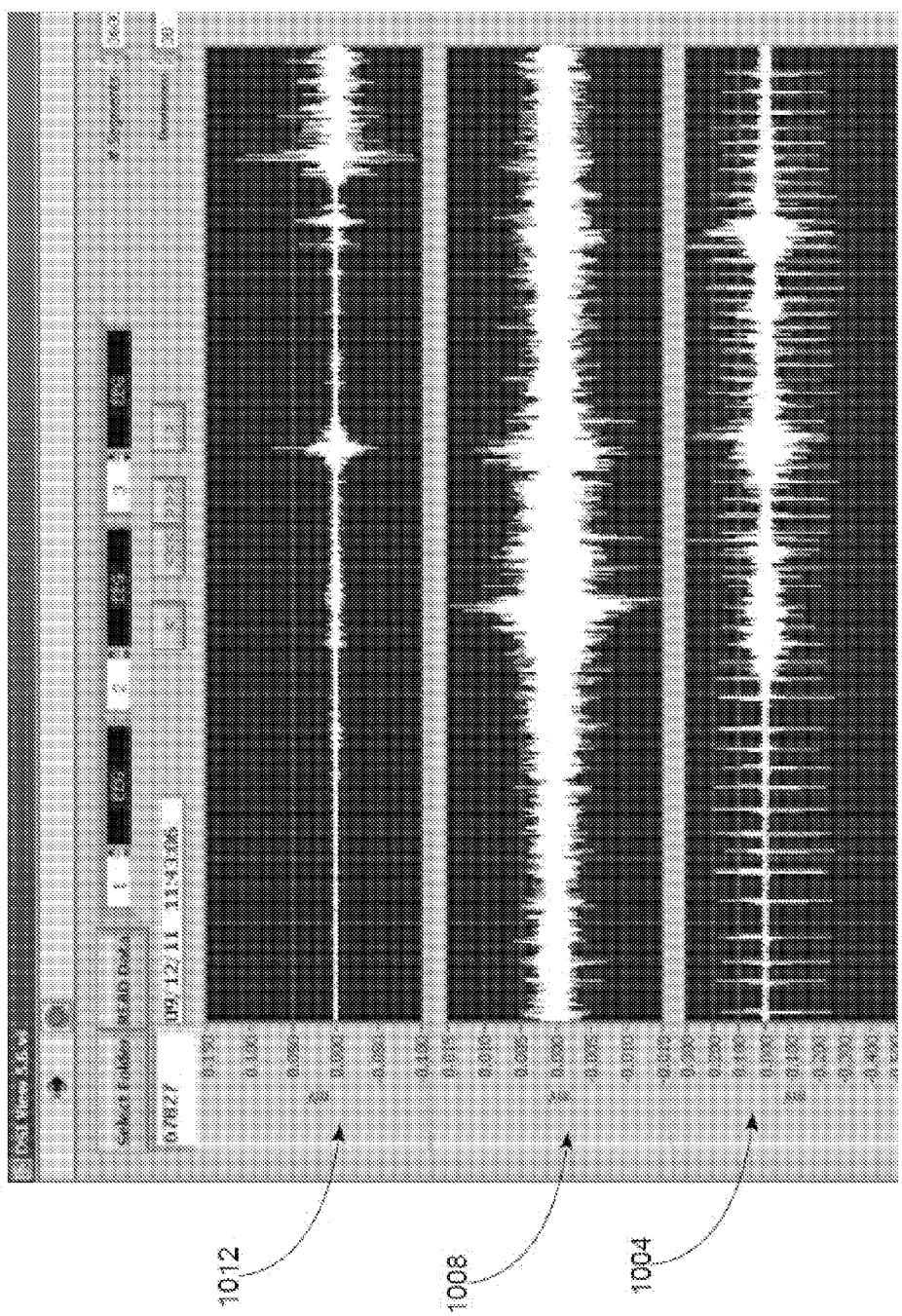
FIG. 10 is a set of graphs recorded by subcutaneous electrodes of a canine subject, depicting a relationship between electrical activity in nerves that are near the skin of a canine subject and an acceleration in the heart rate of the subject.

FIG. 10 depicts three graphs 1004, 1008, and 1012 corresponding to nerve activity in a canine test subject. The graph 1004 depicts nerve activity measured with subcutaneous electrodes that are implanted under the skin of a canine test subject proximate to nerves that innervate the skin, including sympathetic nerves. The graph 1008 depicts nerve activity that is measured with electrodes that are implanted in the thoracic cavity of the canine test subject to monitor the thoracic vagal nerve. These internally implanted electrodes are stainless steel electrodes that conduct electrical signals from the inside of nerve structure to the recording device in the body. The graph 1012 depicts nerve activity that is measured with another set of electrodes that are implanted in the thoracic cavity of the canine test subject to monitor stellate ganglion nerve activity.

In FIG. 10, the graph 1012 depicts sympathetic nerve activity in the stellate ganglion measured directly from the left stellate ganglion, and the graph 1008 depicts a mixture of sympathetic and parasympathetic nerve activity in the vagal thoracic nerve measured directly in the heart. By contrast, the graph 1004 depicts the NECG signal that is detected from the subcutaneous electrodes in nerves that are proximate to the skin of the canine test subject. The subcutaneous electrodes are much less invasive than the needle electrodes that are implanted near the heart, but as depicted in the graphs 1004-1012, the NECG graph 1004 shows increased nerve activity in the subcutaneous nerves during periods of increased sympathetic nerve activity in the stellate ganglion and vagal thoracic nerve.

Figure 11:
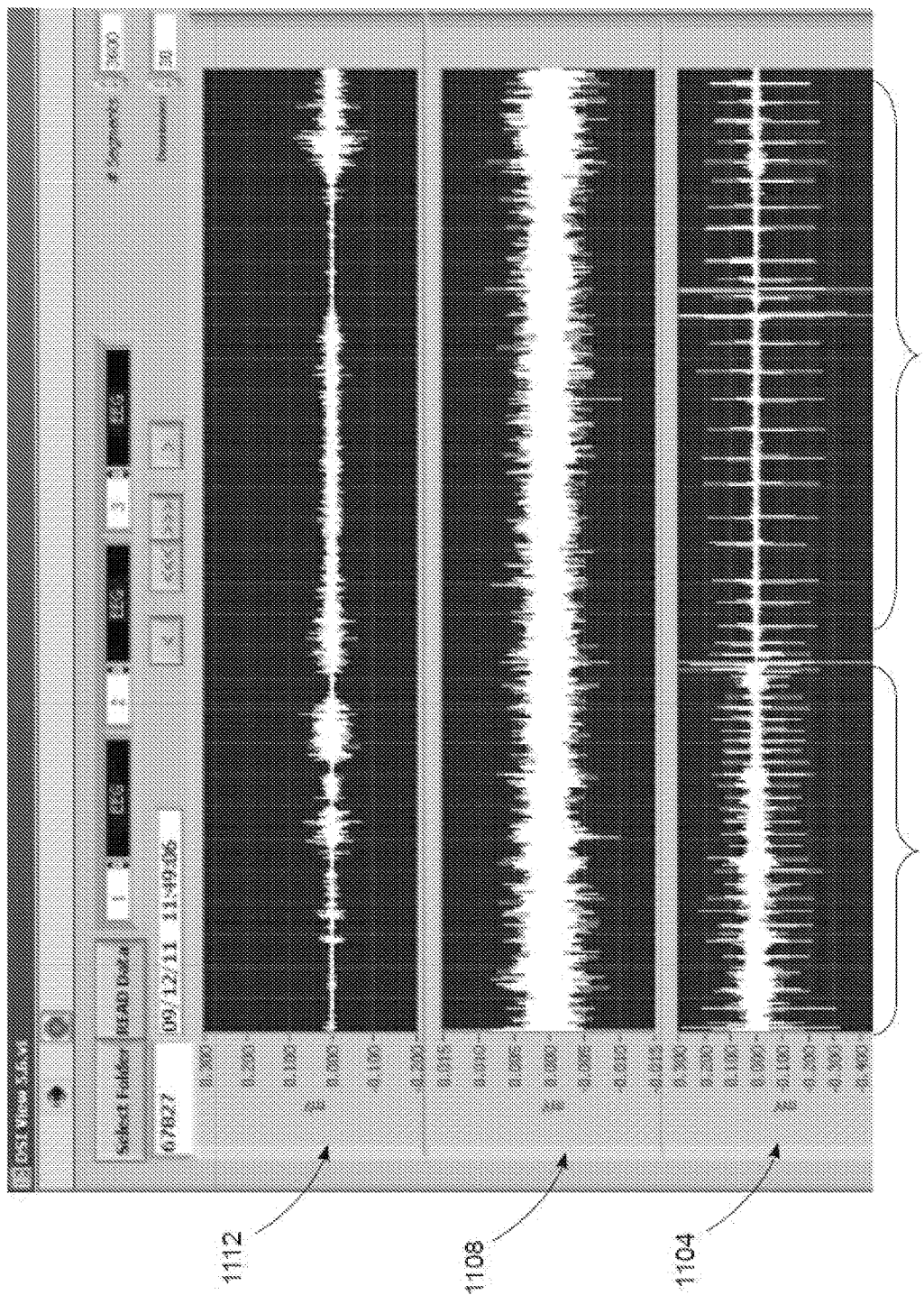
FIG. 11 is another set of graphs recorded by subcutaneous electrodes of a canine subject, depicting a relationship between electrical activity in nerves that are near the skin of a subject and an acceleration in the heart rate of the subject.

FIG. 11 depicts graphs 1104, 1108, and 1112 with the same configuration of electrodes that are described above with reference to the graphs 1004, 1008, and 1012, respectively, in FIG. 10. In FIG. 11, the canine test subject experiences tachycardia. In FIG. 11, the graph 1104 shows increases in overall NECG activity during periods of increase sympathetic nerve activity in the graph 1112, which measures activity in the stellate ganglion. The NECG graph 1104 also depicts the tachycardia in the distance between spikes in the NECG graph 1104 that correspond to the R-wave peaks in the ECG are closer together in time during periods of tachycardia, and farther apart as the heart rate of the test subject slows. For example, in region 1120, the heart rate and overall level of NECG activity is greater, while the heart rate and NECG activity both decrease rapidly in the region 1124.

Figure 12:
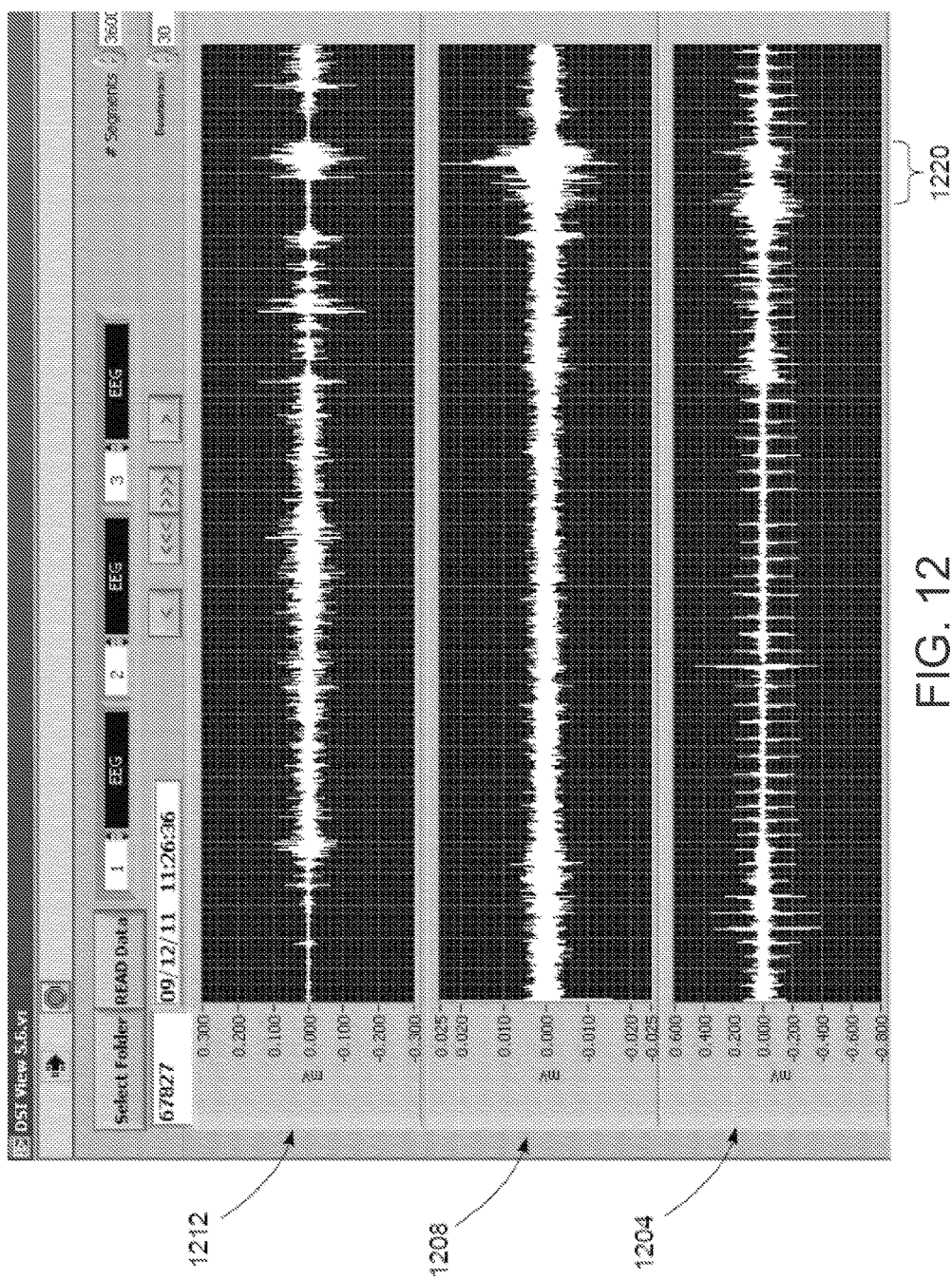
FIG. 12 is another set of graphs recorded by subcutaneous electrodes of a canine subject, depicting a relationship between electrical activity in nerves that are near the skin of a subject and a deceleration in the heart rate of the subject.

FIG. 12 depicts graphs 1204, 1208, and 1212 with the same configuration of electrodes that are described above with reference to the graphs 1204, 1208, and 1212, respectively, in FIG. 10. In FIG. 12, a large increase in the combined sympathetic and parasympathetic nerve activity in the graph vagal nerve graph 1208 in the region 1220 corresponds to a reduction of the heart rate in the NECG graph 1204. While the subcutaneous electrodes in the test subject that monitor nerves that innervate the skin detect many signals from nerves in the sympathetic nervous system, the increased activity in the vagal nerve when the heart slows includes a combination of sympathetic and parasympathetic nerve activity. The subcutaneous electrodes receive electrical signals from the sympathetic nerves that innervate the skin corresponding to the increased activity in the vagal nerve.

Figure 13:
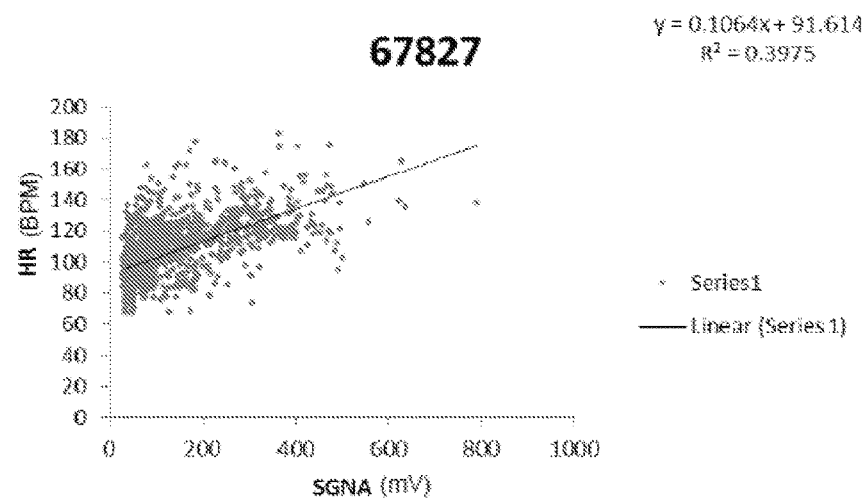
FIG. 13A is a graph depicting a relationship between nerve activity in a stellate ganglion nerve bundle and heart rate in a canine subject.
FIG. 13B is a graph depicting a relationship between nerve activity in a vagal nerve bundle and heart rate in a canine subject.
FIG. 13C is a graph depicting a relationship between nerve activity measured by subcutaneous electrodes and heart rate in a canine subject.
Figure 13:
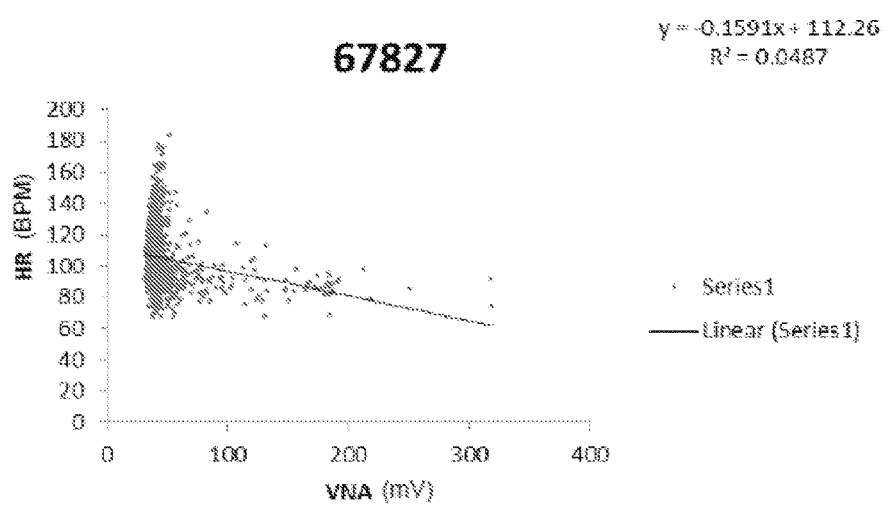
Figure 13:
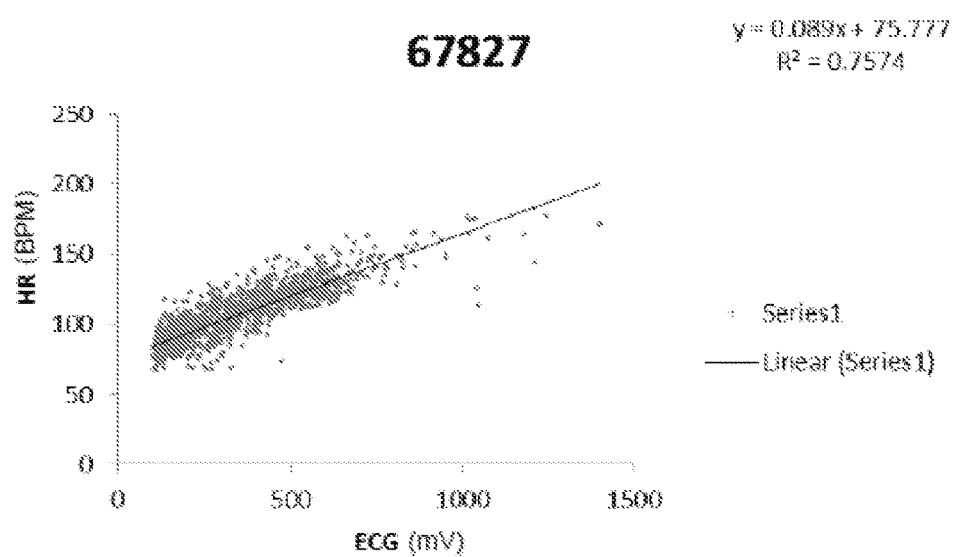

FIG. 13A-FIG. 13C depict relationships between sympathetic nerve activity, vagal nerve activity, ECG activity, and the heart rate in a test subject. Each dot represents the integrated nerve activity or average heart rate within a one-min window. The entire graph consists of data obtained from a 24-hr (1440 min) period. FIG. 13A depicts a positive correlation between an increase in electrical activity in the stellate ganglion, which is a sympathetic nerve, and an increase in the heart rate. FIG. 13B depicts a negative correlation between an increase in the electrical activity in the thoracic vagal nerve fiber, which includes parasympathetic nerves and sympathetic nerves, and a decrease in the heart rate. FIG. 13C depicts a positive correlation between an increase in the average amplitude of an NECG signal and the heart rate. In the monitoring system 100, the subcutaneous or cutaneous electrodes record electrical activity in the nerves that innervate the skin. As depicted in the graphs above, the monitoring system 100 identifies and monitors the NECG signal that includes components corresponding to activity in the autonomic nervous system, and to the ECG. Thus, for many medical treatments including diagnostic and prognostic procedures, the systems and methods described above for monitoring NECG enable non-invasive monitoring of nerve activity in patients and other subjects. The NECG monitoring is either non-invasive when using cutaneous electrodes, and less invasive than existing microneurographic techniques when using subcutaneous electrodes. The NECG monitoring enables long-term monitoring of nerve activity in ambulatory patients for use in monitoring patient health and for control of medical devices to reduce the symptoms of different medical conditions in patients.

The above-described systems and methods may be further understood by way of examples. These examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, certain electrode arrangements and configurations are presented, although it may be understood that other configurations may be possible, and still considered to be well within the scope of the present invention. Likewise, specific process parameters and methods are recited that may be altered or varied based on variables such as signal amplitude, phase, frequency, duration, and so forth.

Example I

The skin is well innervated by sympathetic nerves. Preclinical studies on ambulatory dogs were performed to show whether subcutaneous nerve activity (SCNA) is a good measure of sympathetic tone Surgery was performed to implant radiotransmitters in ambulatory dogs to record left stellate ganglion nerve activity (SGNA), left thoracic vagal nerve activity (VNA), and SCNA from widely spaced bipolar electrodes in the subcutaneous space of the left thorax. After recovery, the radiotransmitter was turned on to continuously record signals from the electrodes at a rate of 1 KHz.

To optimize nerve signals and to filter out any residual ECG signals, data from the left stellate ganglion, the left thoracic vagus nerve, and the subcutaneous tissue were high-pass filtered at 150 Hz and simultaneously displayed with the low pass (100 Hz) filtered ECG from subcutaneous recording. Manual analysis was performed on data streams of baseline recording for all 7 dogs. The data streams were manually analyzed between the hours of 12:00 am and 2:00 am on any given baseline recording day. Episodes of supraventricular (sinus or atrial) tachycardia were defined as heart rate exceeding 150 bpm with narrow QRS complexes. The first 10 tachycardia episodes in which the recordings showed no evidence of noise or motion artifacts were selected for analysis.

Signals resembling nerve activities were consistently observed in the subcutaneous space. There was a significant positive correlation between SGNA and SCNA, with r values of 0.70 (95% confidence interval, CI, 0.61 to 0.84) in these 7 dogs (p<0.05 for each dog). The r value between SCNA and heart rate (0.74, 95% CI 0.68 to 0.80) was significantly (p=0.007) higher than the r value between SGNA and heart rate 33 (0.56, 95% CI 0.45 to 0.67). For analyzed episodes in which heart rate exceeded 150 bpm, it was found that both SGNA and SCNA invariably preceded the tachycardia episodes. There was a significant circadian variation (p<0.05) of both SCNA and SGNA in all dogs studied, but VNA did not show a significant circadian variation. Crosstalk between electrodes was ruled out because SGNA, VNA and SCNA bursts occurred at different times.

Seven adult male mongrel dogs (weighing 20 to 30 kg) were studied to determine the effects of cervical vagal nerve stimulation on left SGNA. The baseline recording (i.e., recording made prior to vagal nerve stimulation) was analyzed test whether subcutaneous nerve activity (SCNA) is a good measure of sympathetic tone in ambulatory dogs. A vagal nerve stimulator (VNS Therapy System; Cyberonics Inc, Houston, Tex.) was implanted to the left cervical vagal nerve. Subsequently, a left thoracotomy was performed through the 3rd intercostal space for the implantation of a radiotransmitter (D70-EEE, Data Sciences International, St. Paul, Minn.). The first pair of electrodes was inserted beneath the fascia of the left stellate ganglion. A second pair of bipolar leads was attached to the left thoracic vagal nerve 2 to 4 cm above the aortic arch. A third pair of bipolar electrodes was placed in the subcutaneous space, with one electrode each inserted under the subcutaneous tissue of left thorax and left lower abdomen. The transmitter and remaining wires were inserted into a subcutaneous pocket. After 2 weeks of recovery, the radiotransmitter was turned on for baseline recording.

Recordings were analyzed from all channels using custom-made software. The subcutaneous recording was low pass filtered at 100 Hz to optimize the visualization of the electrocardiogram (ECG) signals. The ECG signals were analyzed by the software to determine HR. To optimize nerve signals and to filter out any residual ECG signals, data from the left stellate ganglion, left thoracic vagus nerve, and subcutaneous tissue were high-pass filtered at 150 Hz and simultaneously displayed with the low pass filtered ECG. Manual analysis was performed on data streams of baseline recording for all 7 dogs. The data streams were analyzed between the hours of 12:00 am and 2:00 am on any given baseline recording day. This was done to minimize the risk of motion artifact from the animal. HR that exceeded 150 bpm is considered tachycardia. 10 tachycardia episodes per dog were selected for recordings showing no evidence of noise or motion artifacts, and SCNA and SGNA were compared in relation to HR increases and decreases.

In addition to manual analyses, quantitative analyses was performed by integrating the nerve activity min-by-min over 24-hr period during baseline recording. The analysis was started at 12:00 am of one day and finished at 12:00 am of the following day. This was done to help understand the variation of nerve activity in its relation to circadian rhythms. Within the 24 hour period, 3 data streams of nerve activity (SCNA, VNA, and SGNA) were integrated every 60-s at a high pass filter frequency of 150 Hz. This was to help eliminate any residual ECG signals or low frequency artifacts that would contaminate the nerve activity. The integrated nerve activity was plotted against each other to determine the relative nerve activation patterns. {Shen, 2011 #11433} {Shinohara, 2011 #11682}.

Pearson correlation coefficients between heart rate, SCNA, SGNA, and VNA were calculated for each dog and 95% confidence intervals were calculated for the average correlation coefficient using all dogs. A paired t-test was used to compare the average correlation between heart rate and SCNA with heart rate and SGNA between all of the dogs. A cubic smoothing spline was used to fit nerve activity measurement as a function of time over the 24-hr period for each dog. A generalized additive mixed-effects model was used to fit the same data of all dogs. All analyses were performed in SPSS and R software. A two-sided p value of 0.05 was considered statistically significant.

Figure 16:
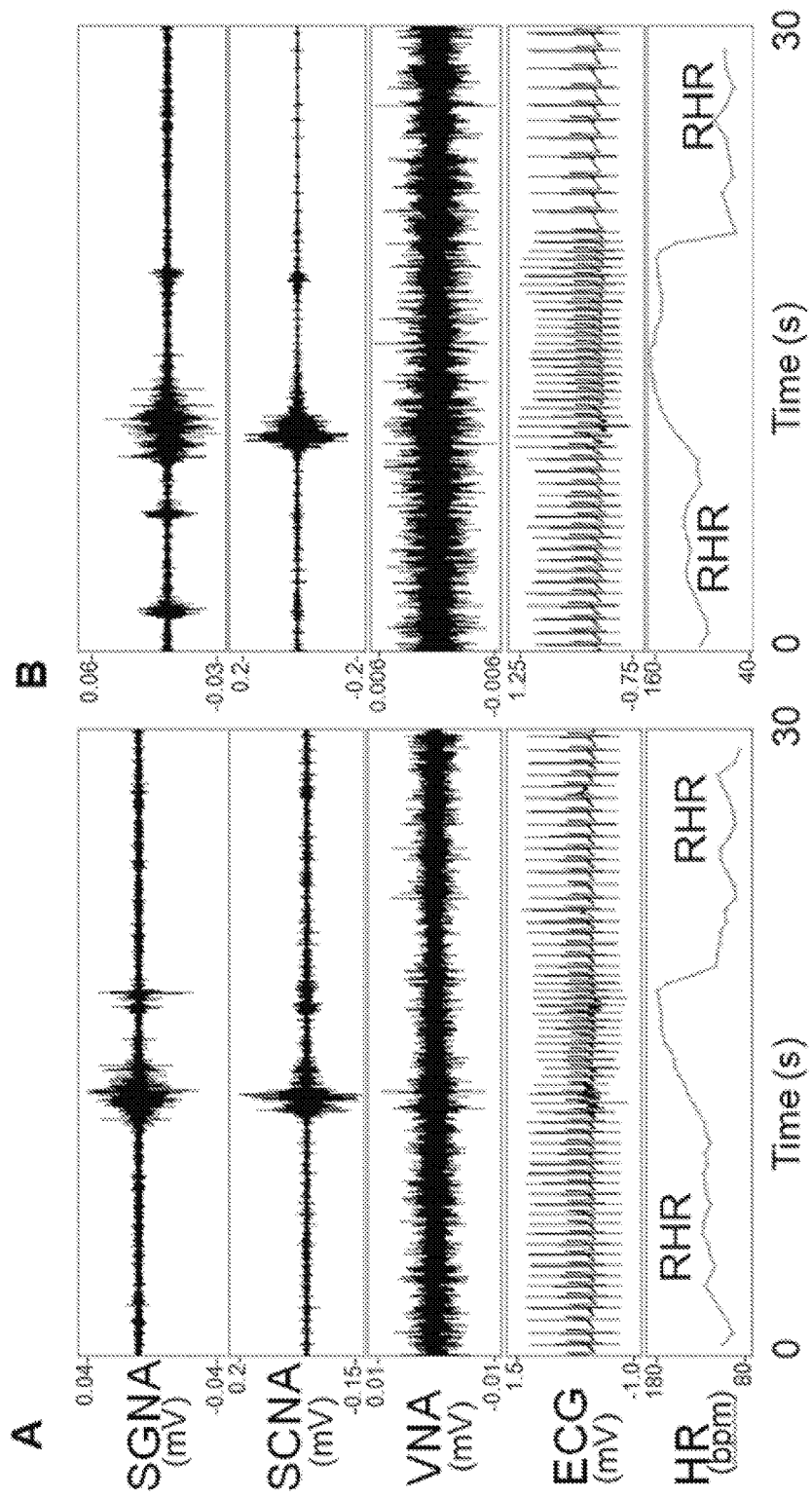
FIG. 16 shows that both SGNA and SCNA activate simultaneously, and that their activations are associated with HR acceleration.

FIG. 16 depicts concordant activation of SCNA and SGNA, associated with heart rate elevation. FIG. 16A shows rhythmic heart rate (HR) variations consistent with respiratory heart rate responses (RHR). SGNA and SCNA are then activated simultaneously, resulting in heart rate acceleration. There were no obvious changes of VNA in this recording. Simultaneous cessation of the SGNA and SCNA was associated with a reduction of the heart rate and the resumption of RHR. FIG. 16B shows simultaneous activation of SGNA, SCNA in the same dog 25 seconds after FIG. 16A.

Figure 17:
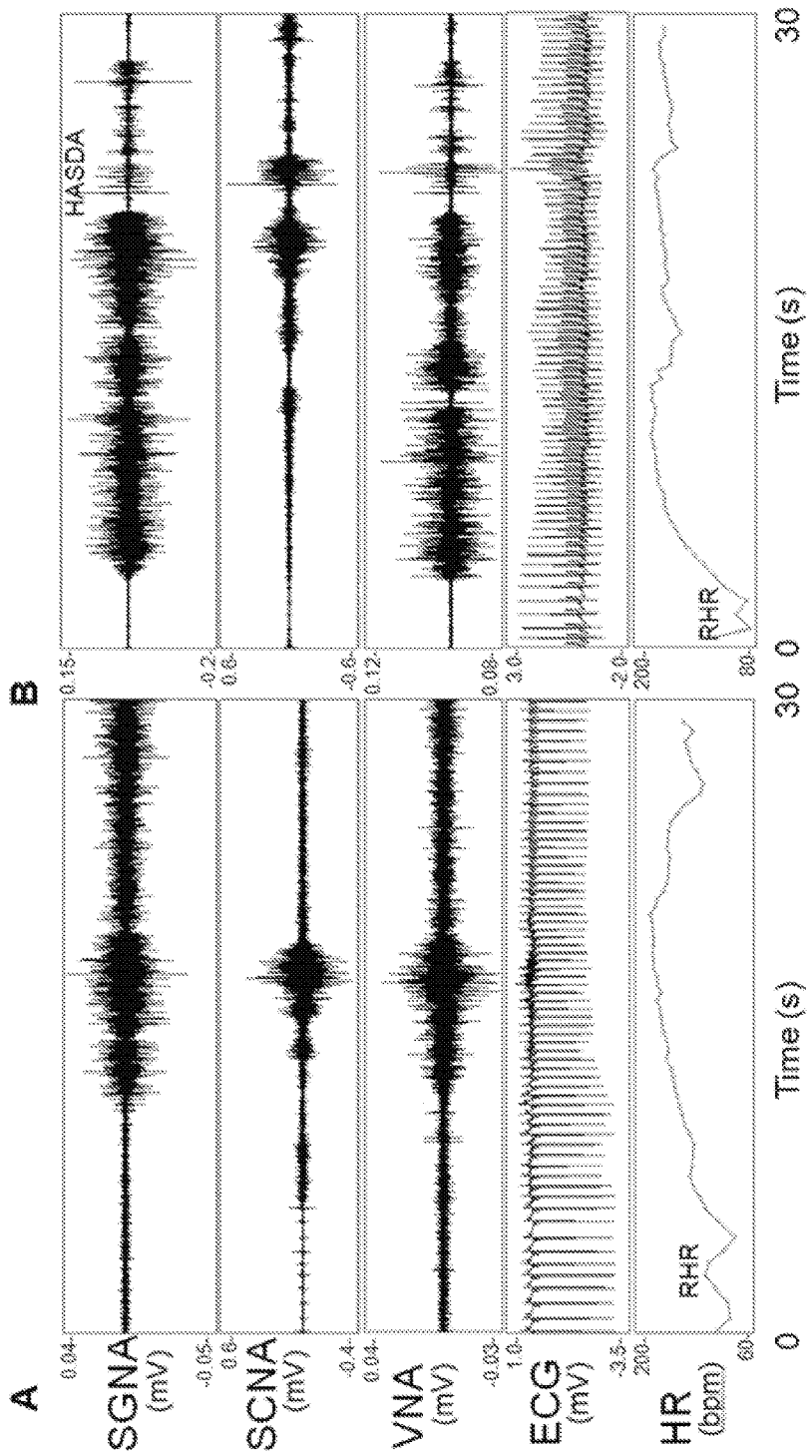
FIG. 17 shows SCNA activates independently of SGNA.

FIG. 17 depicts discordant activation of SCNA and SGNA, and persistent heart rate acceleration. FIG. 17A shows the onset of SCNA initiated persistent heart acceleration for over 20 s. In this episode, the SGNA and VNA occurred after SCNA. Reduction of these nerve activities was followed by heart rate deceleration. FIG. 17B shows SGNA, SCNA and VNA had nearly identical times of onset and offset. However, the morphology of SCNA differed considerably with that recorded in the SGNA and VNA channels. The SGNA signal exhibited high amplitude spike discharge activity (HASDA). These findings were inconsistent with the presence of cross talk among channels.

FIG. 18A shows intermittent heart rate elevation consistent with RHR. Multiple bursts were observed in the SCNA channel that correlated with increases in HR. These episodes were not associated with corresponding SGNA activation. FIG. 18B shows data from the same dog where intermittent nerve electrical activities were associated with RHR, and large nerve discharges occurred simultaneously in all 3 recording channels. shows SCNA activates independently of SGNA.

Figure 19:
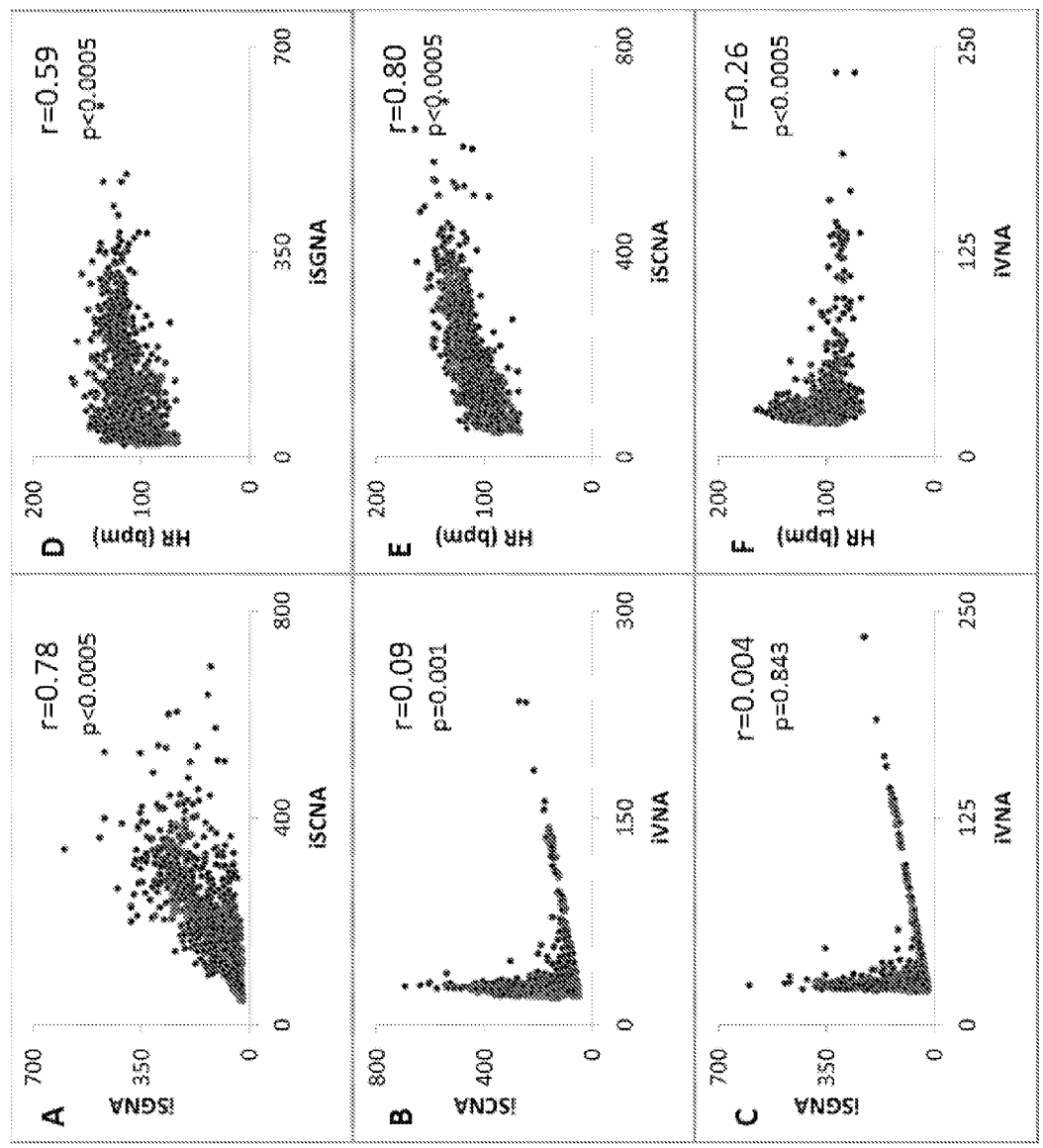
FIG. 19 shows relationship between integrated nerve activities and HR over 24-hr period in a representative dog.

FIG. 19 depicts relationship between integrated nerve activities and HR over 24-hr period in a representative dog. Each dot represents the integrated nerve activity (mV-s) or HR (bpm) over one min. FIG. 19A shows a positive correlation between integrated SGNA (iSGNA) and integrated SCNA. FIG. 19B shows an L-shaped correlation between iSCNA and iVNA. FIG. 19C shows an L-shaped correlation between iSGNA and iVNA. FIG. 19D shows HR correlate positively with iSGNA. FIG. 19E shows HR correlates positively with iSCNA. Note that the correlation coefficient in FIG. 19E is better than that in FIG. 19D. FIG. 19F shows a poor correlation between HR and iVNA.

Figure 20:
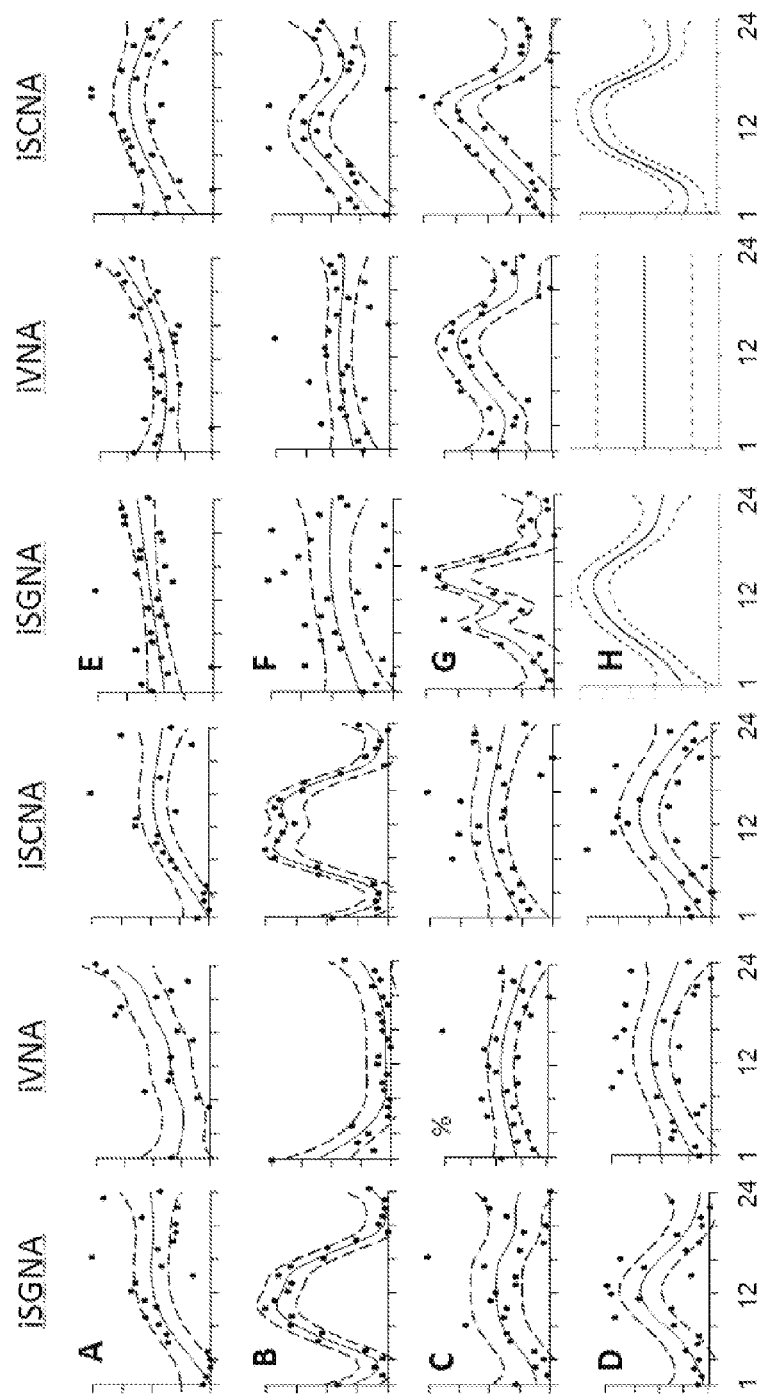
FIG. 20 shows circadian variation of iSCNA, iSGNA, and iVNA.

FIG. 20 depicts circadian variation of iSCNA, iSGNA, and iVNA. A 24-hour period was measured for all seven dogs (FIG. 20A-G). The aggregate data are shown in Panel FIG. 20H. The iSCNA showed significant (p<0.05) circadian variation in all 7 dogs, while significant circadian variation was seen in 6 dogs in iSGNA (all but dog E), and only 2 dogs (dogs C and D) in iVNA. From the aggregate data, it can be shown that both iSCNA and iSGNA have a circadian pattern to them, while iVNA does not have circadian variation.

FIG. 21 depicts Pearson correlations between nerve activities and heart rates. The correlation between iSGNA and iSCNA was positive for all dogs studied.

Increased sympathetic nerve activity is a trigger of cardiac arrhythmias. It was tested that it is feasible to record sympathetic nerve activity subcutaneously in ambulatory dogs, and that subcutaneous sympathetic nerve activity (SCNA) is associated with the development of spontaneous ventricular tachycardia (VT) and ventricular fibrillation (VF).

Electrical signals resembling nerve activity were observed in the subcutaneous tissues. These electrical signals (SCNA) may occur either concordantly or discordantly with the SGNA. FIG. 16 shows typical examples of concordant nerve activities from 2 different dogs. FIG. 16A shows SGNA and SCNA activate simultaneously, leading to an increased HR. There is no VNA in this example. FIG. 16B shows SGNA, SCNA and VNA activate simultaneously and are associated with HR acceleration. The cervical and thoracic vagal nerves have sympathetic components. Therefore, VNA may be associated with HR acceleration. {Onkka, 2013 #12169}

Figure 18:
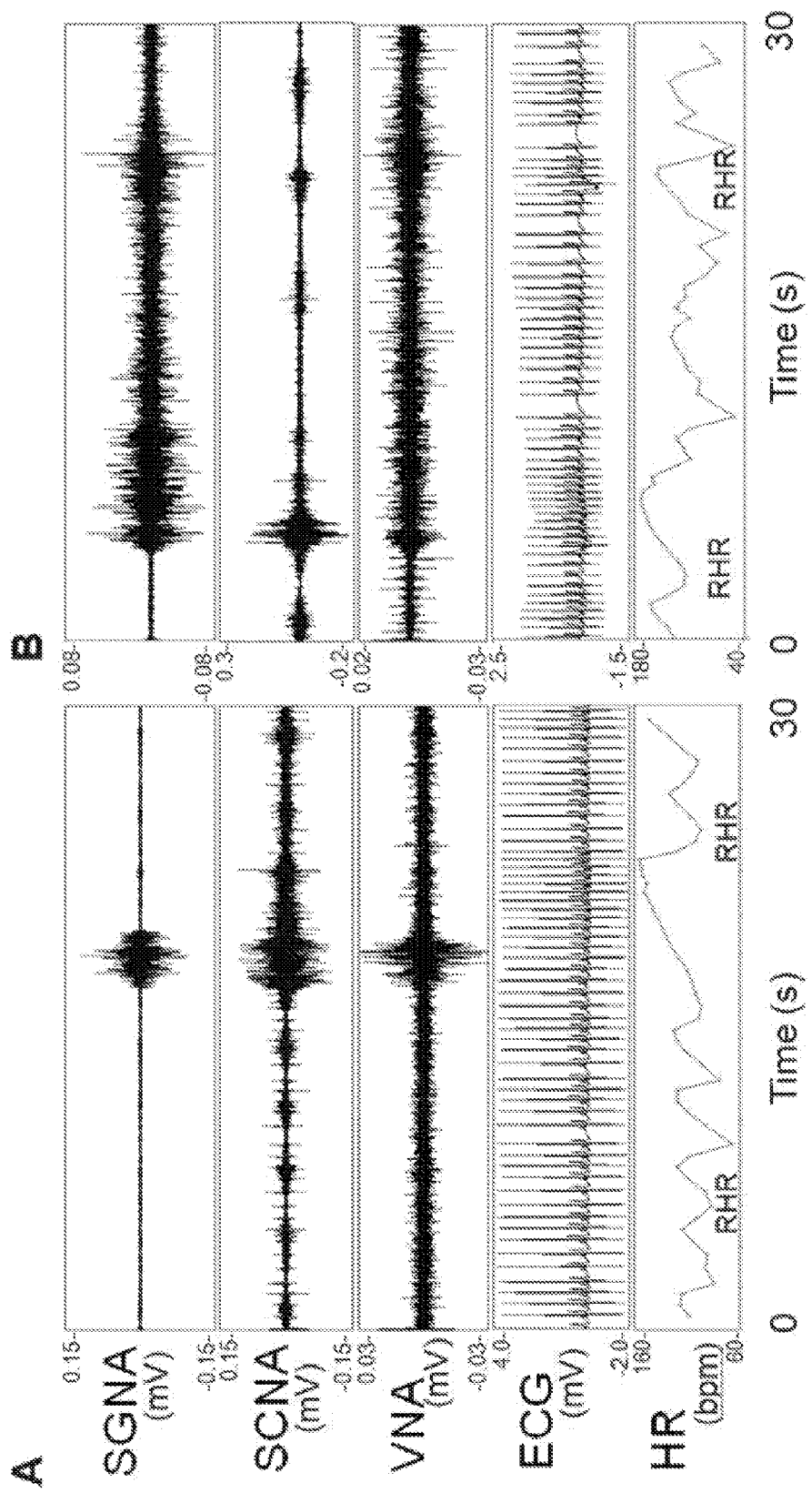
FIG. 18 shows discordant activation of SCNA and SGNA.

FIG. 17 and FIG. 18 depicts examples of discordant SGNA and SCNA, where one activates in the absence of the other. FIG. 17A shows multiple SCNA episodes with only one SGNA episode. Note that there are HR acceleration following SCNA, in spite of the absence of SGNA. FIG. 17B shows intermittent SCNA associated with intermittent HR acceleration. There was no evidence of SGNA in this episode. FIG. 18 shows additional discordant episodes. FIG. 18A shows persistent SGNA but intermittent SCNA. The latter was associated with intermittent transient HR acceleration. FIG. 18B depicts similar findings to FIG. 17, where SCNA and VNA are associated with HR acceleration, even though SGNA is only found in one discreet burst. Among a total of 70 episodes manually analyzed for the timing of their burst discharges, 65 can be seen that the bursts between SCNA and SGNA were of different densities, amplitudes, and times. However, SCNA are still correlating to the episodes of tachycardia. Because of these discordant discharges, it is unlikely that the SCNA is a result of the cross talk with SGNA and VNA.

As observed, SCNA usually fires immediately at the initiation of a HR increase, and tapers off when the HR starts to decrease, while SGNA is usually seen firing in the middle of the HR increase and either firing continuously or only tapering slightly once the HR decreases. A good correlation between SCNA bursts and HR acceleration indicates that SCNA is an adequate measurement of sympathetic tone.

Also, integrated SCNA (iSCNA) correlates positively with integrated SGNA (iSGNA) in all dogs analyzed. FIG. 19A shows the SGNA plotted against SCNA in one dog, showing an r value of 0.78 (p<0.0005). The average r value for all dogs studied was 0.70 (95% CI 0.61 to 0.84). The correlation between iSGNA and iSCNA was positive for all dogs studied (FIG. 21). The iSCNA and iVNA correlation show an L-shaped pattern (FIG. 19B), as did the correlation between iSGNA and iVNA (FIG. 19C). The L-shaped correlation was observed in all 7 dogs studied. The latter correlation is expected for a majority of the ambulatory dogs. {Shen, 2011 #11433}. A second set of comparisons is to determine the relationship between HR and nerve activities. As shown in FIGS. 19D and 19E, there is a significant positive correlation between HR and iSCNA, and between HR and iSGNA, respectively. There is a L-shaped correlation between HR and iVNA (FIG. 19F). The r values of these comparisons for all dogs studied are listed in FIG. 21. As shown in FIG. 21, the correlation between HR and SCNA (r=0.74, 95% CI 0.68 to 0.80) is significantly better than the correlation between HR and SGNA (r=0.56, 95% CI 0.45 to 0.67, p=0.007).

Circadian Variation of iSGNA and iSCNA.

We plotted the hourly iSGNA, iSCNA and iVNA over a 24-hour period (FIG. 20A-G). In all 7 dogs, the iSCNA showed a circadian variation, with levels of activity being greatest during the late morning to afternoon hours, and the least during the evening and early morning. The iSGNA showed circadian variation, similar to iSCNA, in 6 of the dogs, with the remaining dog (dog #E) show an activity pattern that was linear throughout the day. In contrast, the iVNA was quite variable, with 2 dogs (C and D) showing circadian variation, but the remaining 5 showed a linear pattern throughout the day. Finally, in FIG. 20 H, the data of all 7 dogs was aggregated over the 24 hour period. It shows that both iSCNA and iSGNA show a circadian variation, while the iVNA showcased a linear pattern throughout the day.

Figure 22:
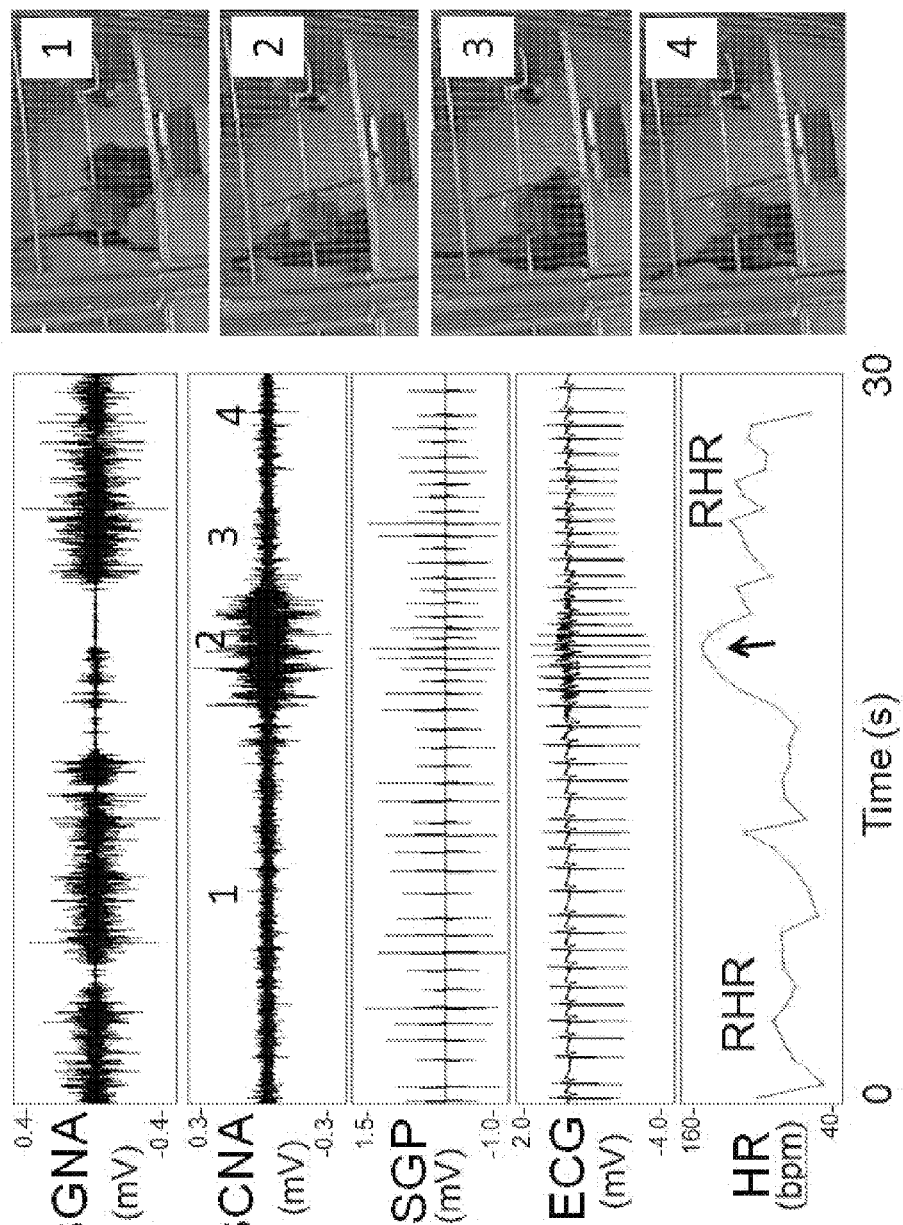
FIG. 22 shows both stellate ganglion nerve activity and subcutaneous nerve activity are present prior to the onset of non-sustained ventricular tachycardia on a simultaneously recorded electrocardiogram (ECG).

FIG. 22 depicts both stellate ganglion nerve activity and subcutaneous nerve activity are present prior to the onset of non-sustained ventricular tachycardia on a simultaneously recorded electrocardiogram (ECG).

Figure 23:
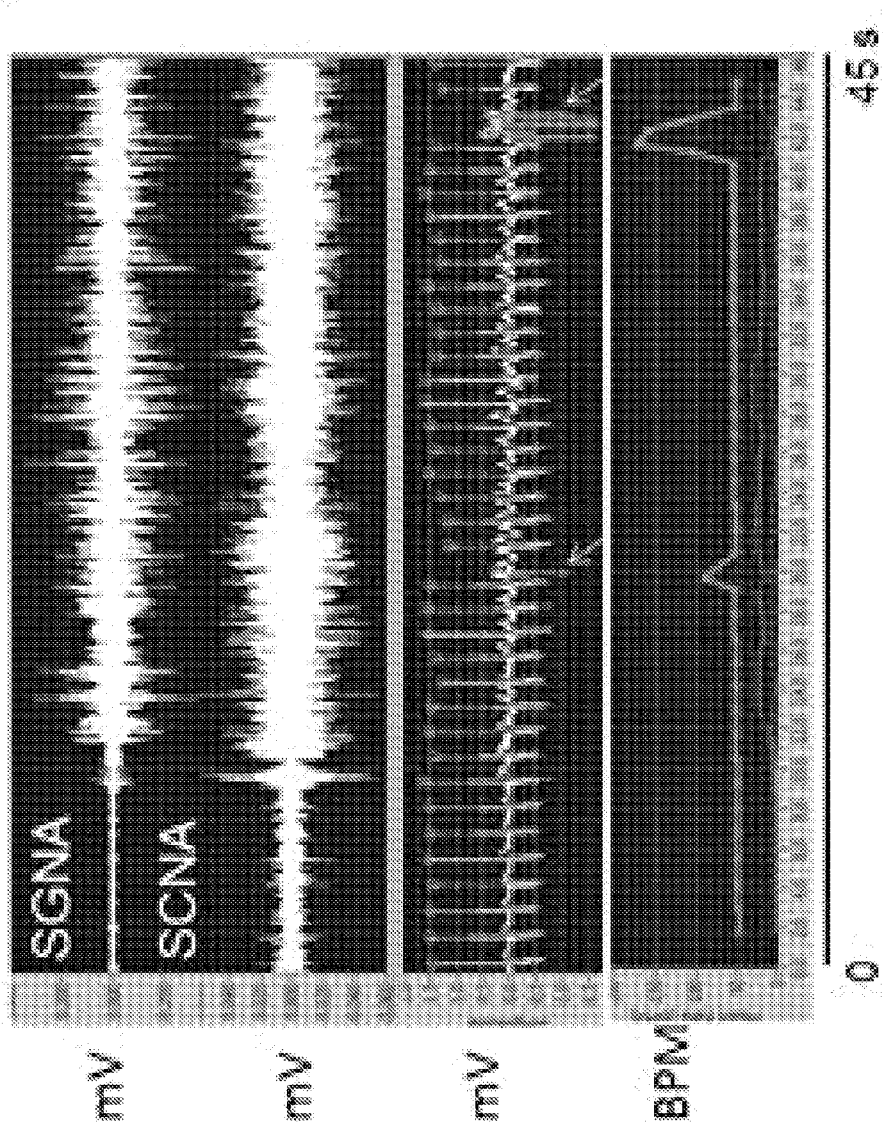
FIG. 23 shows an example of increased nerve activity preceding premature ventricular contractions in a dog.

In addition, simultaneous recording of the nerve activity from the left stellate ganglion (SGNA) and from the thoracic subcutaneous space (SCNA) in 6 ambulatory dogs with complete heart block, myocardial infarction and nerve growth factor infusion to the left stellate ganglion. The electrical signals were sampled at 1 kHz, and high pass filtered at 150 Hz. Two dogs died suddenly of VF. Both VF episodes were preceded by nearly continuous SCNA (32 s and 42 s) and SGNA (38 s and 42 s). There was SCNA within 15 s before 33 (76.7%) of 43 VT, 19 (42.2%) of 45 frequent couplets or bigeminy and 19 (42.2%) of 45 PVCs. An example of increased nerve activity preceding premature ventricular contractions is illustrated in FIG. 23. As shown, both stellate ganglion nerve activity (SGNA) and subcutaneous nerve activity (SCNA) are present prior to the onset of premature ventricular contraction and non-sustained ventricular tachycardia. The SGNA and SCNA signals are not identical, making cross talk between the recording channels unlikely. The second channel and the third channel came from the same data filtered with 150 Hz high pass filter and 100 Hz low pass filter, respectively. The last channel is tachogram. Measured in beats per minute (BPM).

Similar incidence was identified for SGNA (76.7%, 64% and 53.3%, respectively). Significantly progressive increase in integrated SGNA (in mV-s, 76.4±54.7, 82.0±50.5, 95.4±57.7) and SCNA (89.1±50.8, 98.5±52.9 and 111.1±59.3) was observed 60 s, 40 s and 20 s, respectively, prior to VT/VF (p<0.001 for both). This shows that SCNA may be used as a surrogate of SGNA in detecting elevated sympathetic tone that triggers VT and VF in ambulatory dogs.

Example II

To test feasibility of recording signals from electrodes placed on the skin of human patients, simultaneous ECG and SNA were recorded in normal volunteers and nerve activity was correlated with heart rate. Two different sets of data collection hardware were constructed for these studies, The first set of equipment included an ADInstruments (ADI) ML138 OctoBioAmp connected to ten conventional ECG patches for placement at standard locations (RA, RL, LA, LL, and V1-V6), with a wide variety of filters available. This allowed for multiple biopotentials to be recorded from the same subject, such as a 12 lead ECG configuration. The equipment was also supplied with two packets of MLA0310 wires (1.3 m, 10 snap on), suitable for human connection. The signals from the amplifier were digitized by an ADI PowerLab data acquisition system and were recorded continuously on a portable computer.

Patients were typically connected in a 10 or 12-lead ECG configuration, and provocative maneuvers (cold water pressor test and Valsalva) were performed to induce sympathetic nerve discharges. Each provocative maneuver consisted of a control recording period (typically 2 minutes), a recording period during the intervention and a recovery period. Blood pressure and respirations were measured up to every 30 seconds during the provocative maneuvers. The heart rate was monitored continuously via the ECG recordings. Blood pressure, respiratory rate, and heart rate were also measured at the start and end of the study and at the start and end of the rest period. Subjects were asked to avoid muscle contraction or performing a Valsalva maneuver or holding expiration during the tests. Nerve activities were considered present if the signal morphology resembled nerve recordings obtained previously from the stellate ganglion of ambulatory dogs Provocative maneuvers were performed in continuous fashion with 20 minute rest period between each maneuver to allow heart rate, blood pressure, and sympathetic activity to return to baseline as previously described. The cold water pressor test consisted of placing the left hand of a subject in sitting position up to the wrist in ice water for 2 minutes, followed by a 2 minute of recovery period recording. The size of the bucket containing the ice water and the amount of ice and water was kept constant between each participant. For the Valsalva maneuver, subjects were asked to blow into the mouthpiece of a sphygmomanometer and hold the mercury column up to sustain 35 mmHg pressure for a period of at least 30 seconds while in a sitting position. Subsequently, a 2-minute recovery period was recorded.

Figure 24:
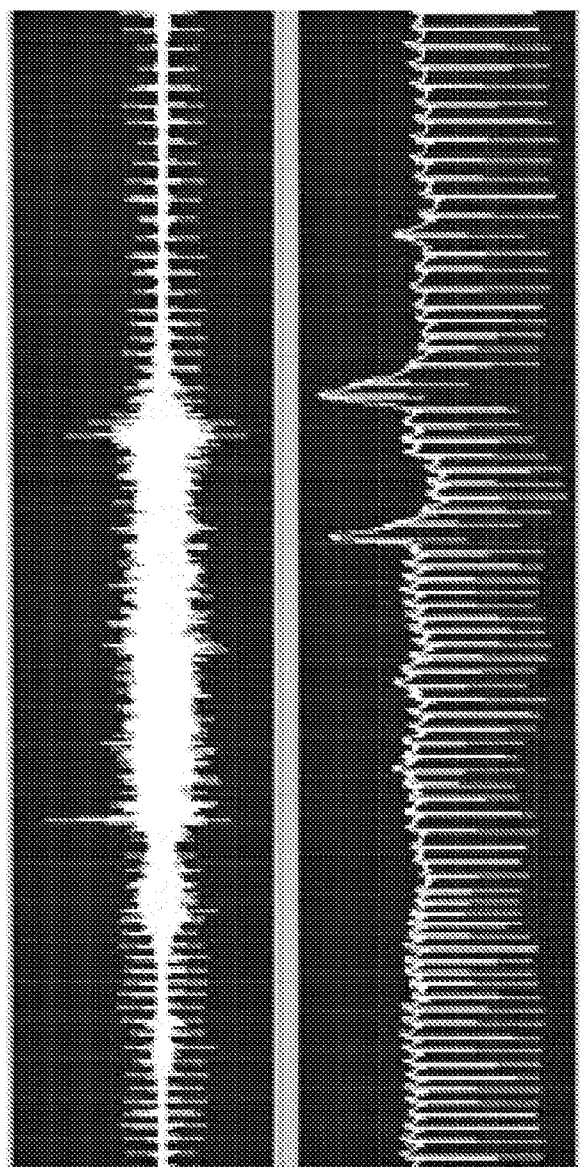
FIG. 24 shows an example of a skin electrode recording during a Valsava maneuver performed on a patient.

Data obtained from four subjects were digitized at 4 kHz, with hardware filter setting of 0.5 Hz high pass and 2 KHz low pass. The 60 Hz Mains Filter was programmed ON. The data were then displayed and analyzed using custom written software developed. Subjects consistently showed an abrupt increase in high frequency electrical activities of surface chest leads. FIG. 24 shows such a recording for a normal volunteer during Valsalva maneuver, where the upper channel is a chest lead (V2) filtered with 100-500 Hz band pass filter and the bottom channel is the same data filtered with a 100 Hz low pass filter, showing ECG.

Since significant muscle tension typically occurs during stressors, such as the Valsalva maneuver, electrical activities recorded on chest leads likely include a combination of nerve and muscle activities. Thus, to eliminate the possibility of local muscle signals, electrodes were placed on the second and third finger of the left hand before, during and after the cold water pressor test. This is because fingers have tendons, blood vessels, subcutaneous tissues and nerves and do not have any skeletal muscle. Further, it is typical to place electrodes on the fingers to perform the sensory nerve conduction velocity studies in humans.

Figure 25:
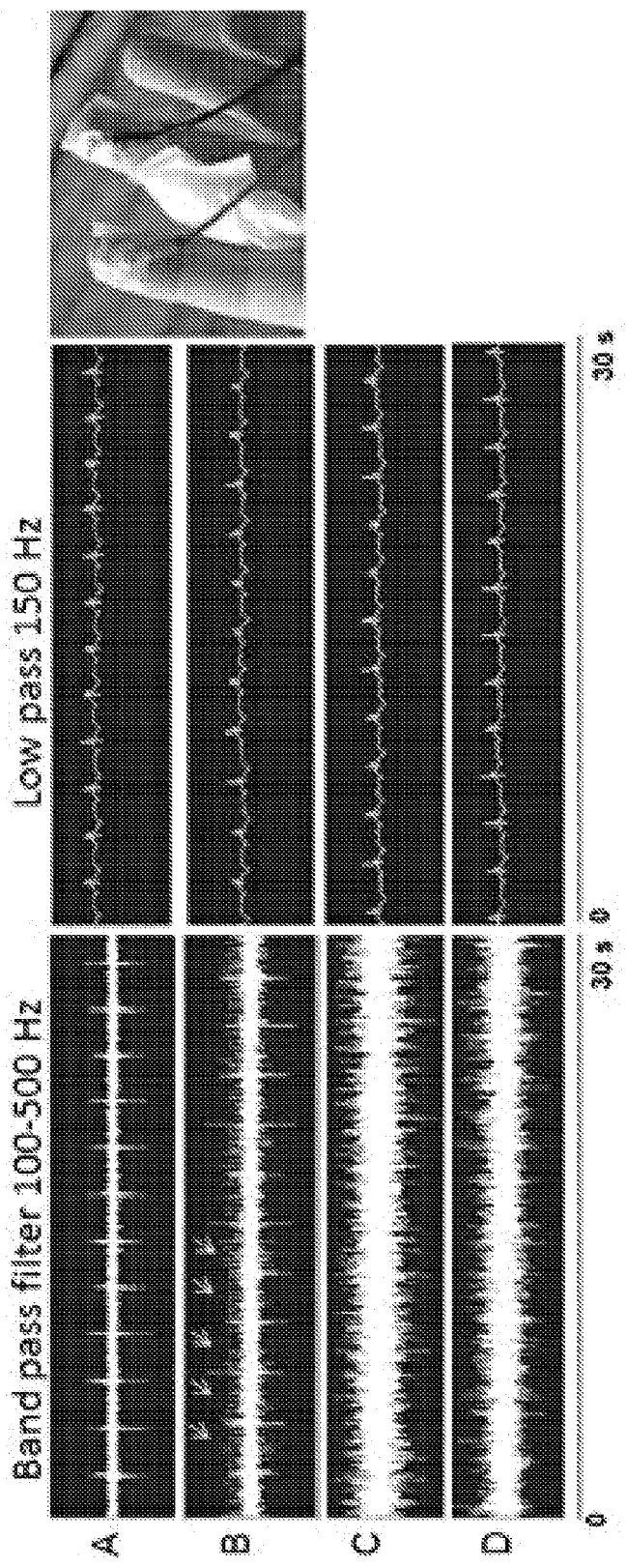
FIG. 25 shows examples of filtered recordings using electrodes placed on the second and third left fingers.

Results shown in FIG. 25 illustrate increased activities on the fingers of the left hand induced by immersion of the right hand in the cold water, with recordings using one electrode on the left second finger and one on left third finger. The SNA (left column) was obtained by band pass filter of 100-500 Hz, while the ECG (right column) was obtained by filtering the same signal with 150 Hz low pass. A is baseline recording, showing sharp spikes corresponding to QRS of the ECG, but no SNA. B shows increased SNA (arrows) 40 s after immersing right hand in ice water. C shows 1 min after immersion, with maximum amount of SNA. D was recorded 1 min into recovery, with continued SNA and heart rate acceleration. The quality of the electrogram resembles that of the nerve activities obtained by standard microneurography techniques, as described. Such results demonstrate that it is feasible to record nerve activities from the chest wall and from fingers.

The right stellate ganglion nerve activity is usually the driver of heart rate acceleration in ambulatory dogs. Because the somata of the subcutaneous sympathetic nerves on the skin are located at the ipsilateral cervical and stellate ganglia, recording SNA from right side should allow a comparison of heart rate changes with SNA. Thus, it may be beneficial to record from the left hand and left chest, and use the right hand for cold water immersion. Also, the left SGNA is known to trigger the onset of cardiac arrhythmias, including AF, VF and VF. SNA recorded from the left hand may be most relevant to the arrhythmogenesis and risk stratification. One electrode, each placed on the ventral surface of the skin overlying the distal phalanx of the second and third fingers, respectively, may be used to form a bipolar recording pair. Another bipolar pair may be placed on the left thoracic chest wall and lower abdomen to record SNA at the locations. The reference electrode may be placed on the thumb to avoid contamination by skeletal muscle. Data may be sampled at 4 kHz, with band width of 1-2K Hz.

Each recording may be digitally processed to separate the SNA signal from the ECG signal. The ECG may be used for HRV analyses to determine the heart rate changes before, during and after cold water stress testing and Valsalva protocols. The software may automatically determine the RR interval, heart rate and display a tachogram along with the ECG. The SNA signal will be processed using methods previously reported for processing microneurography signals. The SNA signals may be filtered and then integrated at 100 ms intervals for continuous display along the filtered signals. Both frequency domain analysis and wavelet analysis may be used to analyze nerve activity and discharges.

To avoid a potential problem with the contamination of the recordings by muscle contractions, especially during a Valsalva maneuver, it may be beneficial to use the frequency distribution of the SNA recorded on the finger as a gold standard. The signal obtained from the chest wall during Valsalva maneuver or during intentional muscle tension may then be compared with the gold standard to design signal processing methods to differentiate between the two.

Figure 26:
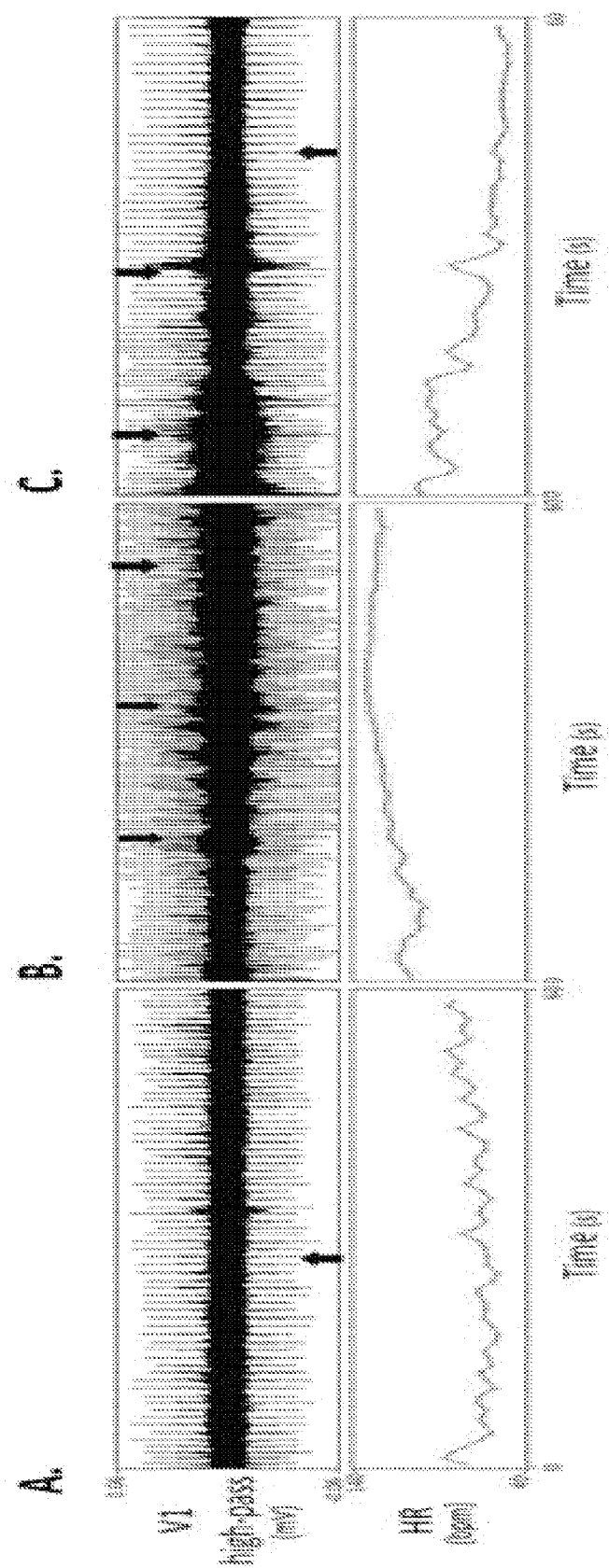
FIG. 26 shows an example of increased sympathetic outflow during a cold water pressor test for a healthy female subject during the control, intervention and recovery periods.
Figure 27:
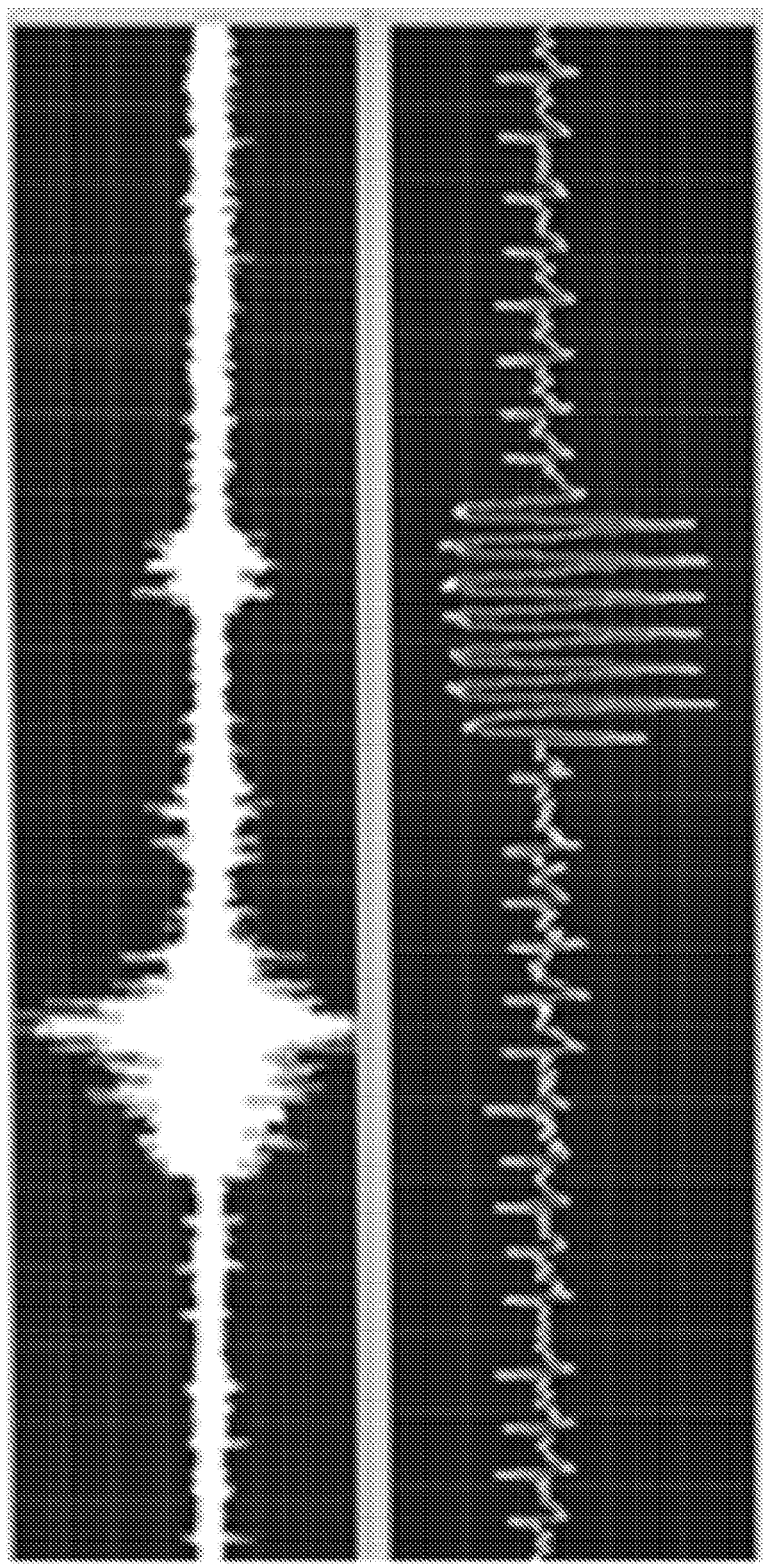
FIG. 27 shows an example recording from a patient with electrical storm showing a non-sustained ventricular tachycardia episode.

Using a liner mixed-effects model, and assuming normality, the integrated nerve activity over 60 second intervals (456 (95% CI 307-606) vs. 332 (95% CI 181-484) mV-s; p=0.01) and mean arterial pressure (92 (95% CI 80-103) vs. 112 (95% CI 101-123) mmHg; p<0.01) for the entire cohort were higher in the intervention compared to the control period. All but one subject had increased nerve discharges during the intervention (downward arrows) and exhibited a negative correlation ($R^2$=0.57 (95% CI 0.48-0.67)) between integrated nerve activity over 30 second intervals and the RR interval. FIG. 26 illustrates increased sympathetic outflow during a cold water pressor test for a healthy female subject during the control, intervention and recovery periods. Given these results, high-pass filtered surface ECG may detect increased sympathetic outflow during the cold water pressor test. This non-invasive method may be useful in measuring sympathetic tone for risk stratification In addition to monitoring normal subjects, the approach of the present invention allows for simultaneously recording ECG and SNA in patients with cardiac arrhythmias, and thus correlate an increase in nerve activity to arrhythmia onset. Thus, recordings from 6 patients known to exhibit electrical storms (ES) were obtained, from which two patients displayed ventricular arrhythmia episodes during recording. ES is a term used to describe a serious clinical condition in which patients have 3 or more separate episodes of ventricular arrhythmias or appropriate ICD therapies over a period of 24 hrs. In both patients, there were high frequency electrical activities prior to the onset of ventricular arrhythmia. FIG. 27 shows an example of high frequency signals preceding the onset of nonsustained VT in a 20 s recording from a patient with electrical storm. The patient had been treated with amiodarone, and was stable without ICD shocks. However, she continued to have episodes of non-sustained VT (lower channel, arrow) preceded by high frequency electrical activities (upper channel, arrows). The filter settings are same as in FIG. 24. The patient had underlying atrial fibrillation with irregular ventricular responses. The high frequency signals had characteristics similar to that shown in canine subcutaneous nerve recordings, with a good signal to noise ratio.

Figure 28:
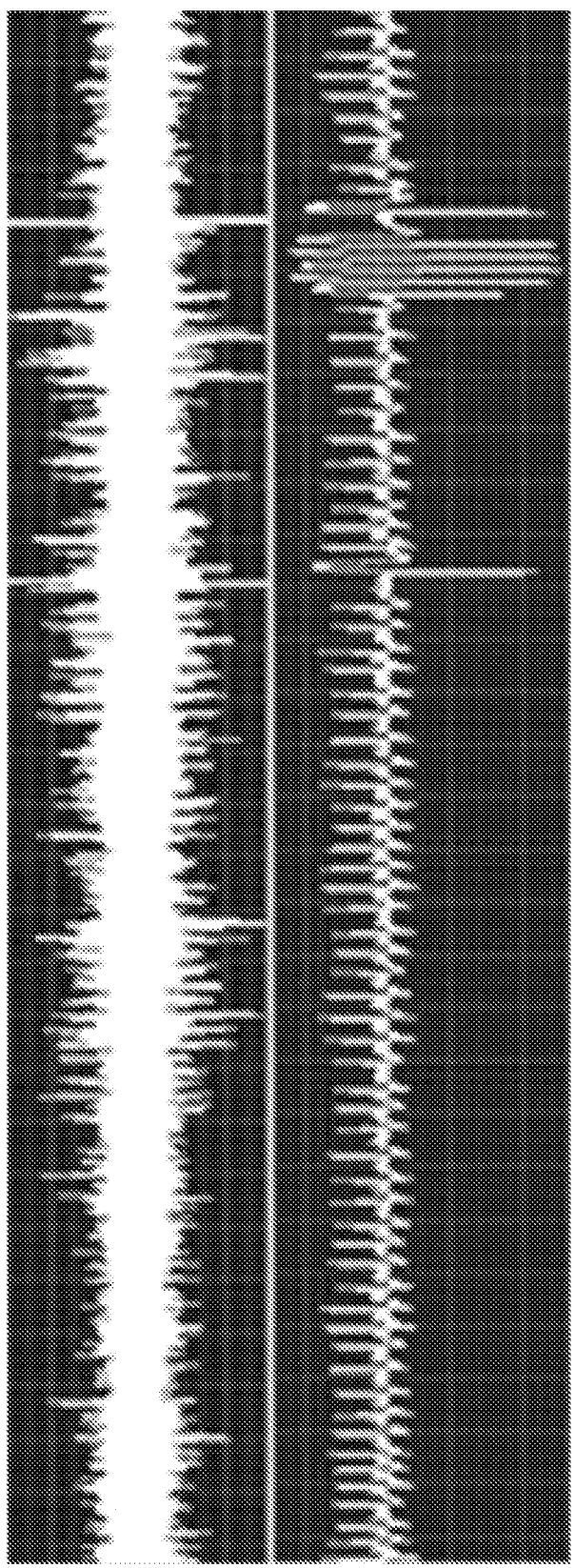
FIG. 28 shows an example recording from a patient showing high frequency signals preceding the occurrence of non-sustained ventricular tachycardia episode.

FIG. 28 shows another episode of VT of the same patient, but on a different day during the same hospitalization, illustrating high frequency signals followed by an episode of non-sustained VT. These observations were similar to the high frequency signals displayed during a Valsalva maneuver using finger tips recordings (FIG. 25). Note that in both FIG. 27 and FIG. 28, high pass filtering was performed to obtain the signals shown in the channel shown in the upper panels. The same signals were low pass filtered to obtain the ECG shown in the lower panel.

According to the above, the systems and methods of the present invention may be applicable to patients admitted for electrical storm. Using for example a portable recording system with two sets of electrode pairs, it may be beneficial to place one set of bipolar electrodes on the right index and middle finger, at the ventral surface of the first phalanx, and a second pair of electrodes on the left side of the chest wall. To avoid muscle contamination, the reference electrode may be placed on the thumb of the left hand. In such configurations, recording may be continuous until the patient is discharged, or may be interrupted for medical necessities.

Similarly, the data may be digitized at 4 kHz, with hardware filter setting of 0.5 Hz high pass and 2 KHz low pass. The 60 Hz Mains Filter may programmed ON to filter out any 60 Hz noise. The signals may be digitally filtered with a 150 Hz high pass filter, and a FFT may be performed on the resulting signal. The FFT may be determined over a 2 second sliding window every 1 second for the duration of the recording. The frequency content of the resulting FFT may then be compared to any nerve discharges within the recording and episodes of accelerated heart rate, VT, or VF. Additionally, muscle noise may be minimized by employing electrodes on the finger tips, which do not have muscle structures, to determine whether recorded chest wall measurements include muscle noise.

The data may be analyzed to determine the association between the high frequency signals with onset of VT. The benchmarks of success may include recording of high frequency signals with the same frequency distribution during cold water pressor test. If this is observed, then these high frequency signals are likely the sympathetic nerve activity, and an association between nerve activity and ventricular arrhythmias, such as premature ventricular contractions, couples and VT. In a canine model of sudden death, 86% of sudden death and VT were preceded within 15 s by SGNA episodes. In the cases of similar high incidence of correlation, then the high frequency signals are most likely sympathetic nerve activities, and nerve activity may be used to predict cardiac arrhythmias.

In summary, cardiovascular disease is a leading cause of death in the United States. Sudden cardiac death (SCD) accounts for approximately 50% of cardiac mortality. Over 80% of SCD occurs in patients with structural heart disease, primarily coronary artery disease and nonischemic dilated cardiomyopathy. Sympathetic tone is important in cardiac arrhythmogenesis and heart rate variability is a commonly used method to estimate cardiac autonomic nerve activities. However, this approach requires proper sinus node response to autonomic stimulation, and since sinus node function may be abnormal in heart failure or atrial fibrillation, heart rate variability parameters may not reflect the sympathetic tone in those conditions. Alternatively, SNA recording performed using microneurography to directly measure SNA in humans. However, such procedures are invasive and typically may not be convenient in ambulatory subjects.

As described by the present inventions, direct recording of autonomic nerve activity has been demonstrated in ambulatory dogs using electrodes placed directly on the stellate ganglion, showing that SNA immediately precedes the onset of atrial and ventricular arrhythmias, as well as sudden cardiac death. For electrodes placed in subcutaneous tissue, analysis of signals recorded in this manner demonstrated that subcutaneous measurements may be used as surrogate of stellate ganglion nerve activity recording to determine the sympathetic tone in ambulatory dogs. It was also discovered that subcutaneous nerve activity consistently precedes the onset of spontaneous ventricular tachycardia (VT) and ventricular fibrillation (VF) in an ambulatory canine model of ventricular arrhythmia and sudden cardiac death.

In addition, ECG and nerve activity was simultaneously measured on the skin of normal volunteers and in patients with postoperative atrial fibrillation (AF) and electrical storm (recurrent VT and VF). The results showed electrical signals consistent with SNA, and that the SNA correlated with heart rate acceleration, atrial fibrillation (AF), VT and VF. Thus, the systems and methods as described by the present invention may be implemented in a diagnostic tool for the prediction of cardiac arrhythmias and sudden cardiac death. In addition, such systems and methods may be beneficial in the diagnosis of diseases involving the peripheral nervous system, such as neuromuscular diseases.

A number of prospective randomized clinical trials have demonstrated the ability of implantable cardioverter-defibrillator (ICD) to reduce mortality in patients with poor left ventricular function that have never experienced symptomatic ventricular arrhythmias (primary prevention), leading to current guidelines that specify patients with left ventricular ejection fraction ≤35% without contraindications should receive ICDs for the primary prevention of SCD. However, while the current guidelines are appealing in their simplicity, there are significant flaws with this approach. Post-hoc analyses of the ICD trials have shown that ICD benefit was not distributed uniformly across the study populations. Because significant numbers of "indicated" patients do not experience improved survival from the ICD, there is room for improvement to select patients for this expensive therapy. Additionally, a majority of sudden death in the community occurs in patients not eligible for primary prevention ICDs.

Therefore, improved methods to determine risk stratification are highly desirable to select patients for SCD prevention. Increased sympathetic tone heightens vulnerability to ventricular arrhythmias, and thus sympathetic nerve activity (SNA) has been shown to be important in cardiac arrhythmogenesis and SCD. Among several measures of sympathetic tone, heart rate variability (HRV) is one of the most commonly used measures. Multiple investigators have employed mathematical tools to study HRV, showing that HRV is an important prognostic parameter for arrhythmias and SCD. However, this approach provides an indirect measure of the sympathetic tone, and is most accurate in patients with normal functioning sinus nodes. Thus, despite many studies, HRV has not been accepted as an effective method in arrhythmia risk stratification.

Baroreflex sensitivity, which combines HRV and blood pressure measurements, allows more effective risk stratification. However, this method is not easy to perform, and has not been accepted by clinicians for risk stratification since it has been shown to have a high negative predictive value and a low positive predictive value in patients with an EF<35%. By contrast, the systems and methods of the present invention allow for directly recording SNA from the skin using conventional electrodes. Such an approach may provide for better arrhythmia risk stratification in patients with heart diseases and thus make a significant impact on patient care.

Since its invention, the electrocardiogram (ECG) has been an important part of clinical practice. To preserve the signal and eliminate noise, the standard recommendation for low pass filtering of the ECG is 150 Hz for adolescents and adults, and 250 Hz for children. Higher frequency signals, although known to be clinically important, are routinely eliminated by low pass filtering. By contrast, in the approach of the present invention useful information may be obtained by recording both low and high frequency signals from the skin. High frequency signals contain SNA, which may be used for clinical risk stratification and arrhythmia prediction. Appropriate data acquisition and processing of both low and high frequency signals allow for detection of both cardiac activity (ECG) and sympathetic nerve activity (SNA) using the same data.

Using recordings on the skin, the systems and methods as described by the present invention may utilize conventional skin electrodes that are widely use in health care facilities, are non-invasive, easy to use, and implement hardware and data acquisitions systems readily available. Such approaches may provide simultaneous recording of sympathetic nerve activity (SNA) and electrocardiogram (ECG) for use in arrhythmia prediction, detection, and intervention, at low cost, allowing for robust commercialization.

Systems and methods as described by the present invention may include signal processing software to automatically eliminate noise, such as that generated by muscle contraction, electrical appliances, body motion, respiration and radiofrequency signals. The remaining signals may then be processed to separately display and analyze the ECG and SNA signals. The ECG signals may be used for automated arrhythmia detection while the SNA signals may be available for risk stratification. This approach allows for maximal utilization of the same signals obtained from the skin, thus providing improvement over traditional technologies.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for monitoring nerve activity in a subject comprising:
   amplifying, using a signal amplifier connected to a plurality of electrodes configured to be placed in proximity to the subject's skin, electrical signals received from the plurality of electrodes to generate a plurality of amplified signals; and
   using a signal processor operatively connected to the signal amplifier:
      applying a high-pass filter to the plurality of amplified signals to generate a plurality of filtered signals, the high-pass filter configured to attenuate a plurality of the amplified signals having frequencies that correspond to muscle activity in the subject;
      identifying nerve activity in the plurality of filtered signals;
      generating an output signal corresponding to the nerve activity in the plurality of filtered signals; and
      activating, based on the output signal, a therapeutic device implanted in the subject to deliver a therapeutic signal to the subject.

2. The method of claim 1 further comprising:
   generating a visual display of the identified nerve activity in the plurality of filtered signals from the output signal.

3. The method of claim 2, wherein the generation of the visual display further comprises:
   integrating, using the signal processor, the identified nerve activity to identify a total magnitude of the nerve activity over a predetermined period of time; and
   generating the visual display including the total magnitude of the nerve activity.

4. The method of claim 1 further comprising:
   identifying an arrhythmia in the heartbeat of the subject with reference to a change in the identified nerve activity and generating an alarm in response to identifying the arrhythmia, using the signal processor.

5. The method of claim 4, wherein the identification of the arrhythmia in the heartbeat further comprises identifying the arrhythmia prior to onset of the arrhythmia in the heartbeat.

6. The method of claim 4, wherein the therapeutic device is a pacing device implanted in the subject and the therapeutic signal is a pacing signal to heart muscle in response to identifying the arrhythmia.

7. The method of claim 4, wherein the therapeutic device is a defibrillator device implanted in the subject and the therapeutic signal is a defibrillation signal to heart muscle in response to identifying the arrhythmia.

8. The method of claim 1, further comprising performing using the signal processor:
   identifying, using the identified nerve activity, a suitability for the subject to receive a therapy aimed at modifying the identified nerve activity; or evaluating an effectiveness of a neuromodulation therapy with reference to a difference in the identified nerve activity, or both.

9. A method for monitoring nerve activity m a subject comprising:
   amplifying, using a signal amplifier, electrical signals received from a plurality of electrodes that are configured to be placed in proximity to skin of the subject to generate a plurality of amplified signals;
   applying, using a signal processor operatively connected to the signal amplifier, a high-pass filter to the plurality of amplified signals to generate a plurality of filtered signals, the high-pass filter configured to attenuate a plurality of the amplified signals having frequencies that correspond to muscle activity in the subject;
   identifying nerve activity in the plurality of filtered signals using the signal processor;
   generating, using the signal processor an output signal corresponding to the nerve activity in the plurality of filtered signals; and
   activating, based on the output signal, a therapeutic device implanted in the subject to deliver a therapeutic signal to the subject.

* * * * *